United States Patent
Martin et al.

(10) Patent No.: US 8,361,760 B2
(45) Date of Patent: Jan. 29, 2013

(54) MICROBIAL PRODUCTION OF 3-HYDROXYACIDS FROM GLUCOSE AND GLYCOLATE

(75) Inventors: Collin Hunter Martin, North Wales, PA (US); Kristala Lanett Jones Prather, Milton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 191 days.

(21) Appl. No.: 12/718,469

(22) Filed: Mar. 5, 2010

(65) Prior Publication Data

US 2010/0255549 A1   Oct. 7, 2010

Related U.S. Application Data

(60) Provisional application No. 61/158,216, filed on Mar. 6, 2009.

(51) Int. Cl.
*C12P 17/04* (2006.01)
*C12P 7/62* (2006.01)
*C12N 1/20* (2006.01)
*C12N 1/00* (2006.01)
*C12N 5/00* (2006.01)
*C12N 5/07* (2010.01)
*C12N 5/04* (2006.01)
*C12N 15/00* (2006.01)
*C12N 15/82* (2006.01)
*C12N 15/74* (2006.01)

(52) U.S. Cl. ............ 435/126; 435/135; 435/252.3; 435/254.11; 435/254.2; 435/325; 435/348; 435/419; 435/455; 435/468; 435/471

(58) Field of Classification Search ............. 435/126, 435/135, 252.3, 254.11, 325, 348, 419, 455, 435/468, 471
See application file for complete search history.

(56) References Cited

U.S. PATENT DOCUMENTS 5,808,107 A    9/1998   Hollingsworth

FOREIGN PATENT DOCUMENTS

| WO | WO 2007/140816 | 12/2007 |
|----|----|----|
| WO | WO 2008/062996 | 5/2008 |
| WO | WO 2009/145840 | 12/2009 |
| WO | WO 2010/101651 | 9/2010 |

OTHER PUBLICATIONS

Greenler et al, isolation and characterization and sequence analysis of full-length cDNA encoding NADH-dependent hydroxypyruvate reductase from cucumber. Plant Mol. Biol., 1989, vol. 13: 139-150.*
Martin et al., High-titer production of monomeric hydroxyvalerates from levulinic acid *Pseudomonas putida*. J. Biotechnol., 2009, vol. 139: 61-67.*
Suriyamongkol et al., Biotechnological approaches for the production of polyhydroxyalkanoates in microorganisms and plants—A review. Biotechnol. Adv., 2007, vol. 25: 148-175.*
Taguchi et al., A microbial factory for lactate-based polyesters using lactate-polymerizing enzyme. PNAS., 2008, vol. 105 (45): 17323-17327.*
Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kimchi-Sarfaty et al., A "Silent" polymorphism in the MDR1 gene changes substrate specificty. Science, 2007, vol. 315: 525-528.*
Kisselev L., Polypeptide release factors in prokaryotes and eukaryotes: same function, different structure. Structure, 2002, vol. 10: 8-9.*
Nackley et al., Human Caechol-O-Methytransferase haplotypes modulate protein expression by altering mRNA secondary structure. Science, 2006, vol. 314: 1930-1933.*
Sauna et al., Silent polymorhisms speak: How they affect pharmacogenomics and the treatment of cancer. Cancer Res., 2007, vol. 67(20): 9609-9612.*
Seffernick et al., Melamine deaminase and Atrazine chlorohydrolase: 98 percent identical but functionally different. J. Bacteriol., 2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
U.S. Appl. No. 13/404,993, filed Feb. 24, 2012, Dhamankar et al.
PCT/US2010/000674, Jun. 18, 2010, International Search Report and Written Opinion.
PCT/US2010/000674, Sep. 15, 2011, International Preliminary Report on Patentability.
PCT/US2012/000674, Aug. 8, 2012, International Search Report and Written Opinion.
Genbank Submission; NCBI; Accession No. AAN67665.1; Nelson et al.; Mar. 5, 2010.
Boynton et al., Cloning, sequencing, and expression of clustered genes encoding beta-hydroxybutyryl-coenzyme A (CoA) dehydrogenase, crotonase, and butyryl-CoA dehydrogenase from *Clostridium acetobutylicum* ATCC 824. J Bacteriol. Jun. 1996;178(11):3015-24.
Boynton et al., Cloning, sequencing, and expression of genes encoding phosphotransacetylase and acetate kinase from *Clostridium acetobutylicum* ATCC 824. Appl Environ Microbiol. Aug. 1996;62(8):2758-66.
Chen et al., Microbial production and applications of chiral hydroxyalkanoates. Appl Microbiol Biotechnol. Jun. 2005;67(5):592-9. Epub Feb. 8, 2005.
Chiba et al., A synthetic approach to (+)-thienamycin from methyl (r)-3-hydroxybutanoate. a new entry to (3r, 4r)-3-[(r)-1-hydroxyethyl]-4-acetoxy-2-azetidinone. Chem Lett. 1985; 14(5):651-4.

(Continued)

*Primary Examiner* — Ganapathirama Raghu
(74) *Attorney, Agent, or Firm* — Wolf, Greenfield & Sacks, P.C.

(57) ABSTRACT

The invention relates to recombinant cells and their use in the production of 3-hydroxyacids such as 3,4-dihydroxybutyrate and 3-hydroxybutyrolactone.

20 Claims, 13 Drawing Sheets

OTHER PUBLICATIONS

Dhamankar et al., Biosynthesis of 3-hydroxy-g-butyrolactone and 3,4-dihydroxybutyric acid in *Escherichia coli* from glucose as a sole feedstock. Am Chem Soc. 2011 Mar. 30, 2011;241:358.

Gao et al., Enhanced production of D-(−)-3-hydroxybutyric acid by recombinant *Escherichia coli*. FEMS Microbiol Lett. Jul. 16, 2002;213(1):59-65.

Huisman et al., Metabolism of poly(3-hydroxyalkanoates) (PHAs) by *Pseudomonas oleovorans*. Identification and sequences of genes and function of the encoded proteins in the synthesis and degradation of PHA. J Biol Chem. Feb. 5, 1991;266(4):2191-8.

Kim et al., Crystal structure of HIV-1 protease in complex with VX-478, a potent and orally bioavailable inhibitor of the enzyme. J Am Chem Soc. 1995;117(3):1181-2.

Lee et al., A chemoenzymatic approach to the synthesis of enantiomerically pure (S)-3-hydroxygamma-butyrolactone. Appl Microbiol Biotechnol. Jun. 2008;79(3):355-62. Epub May 1, 2008.

Lee et al., Biosynthesis of enantiopure (S)-3-hydroxybutyric acid in metabolically engineered *Escherichia coli*. Appl Microbiol Biotechnol. Jun. 2008;79(4):633-41. Epub May 7, 2008.

Lee et al., Fermentative butanol production by Clostridia. Biotechnol Bioeng. Oct. 1, 2008;101(2):209-28.

Lee et al., Production of chiral and other valuable compounds from microbial polyesters Biopolymers, polyesters III. Eds. Dio et al. Wiley-VCH. Weinheim. 2002. p. 375-87.

Lee et al., Uses and production of chiral 3-hydroxy-gamma-butyrolactones and structurally related chemicals. Appl Microbiol Biotechnol. Oct. 2009;84(5):817-28. Epub Aug. 4, 2009.

Liu et al., A novel genetically engineered pathway for synthesis of poly(hydroxyalkanoic acids) in *Escherichia coli*. Appl Environ Microbiol. Feb. 2000;66(2):739-43.

Liu et al., Exploitation of butyrate kinase and phosphotransbutyrylase from *Clostridium acetobutylicum* for the in vitro biosynthesis of poly(hydroxyalkanoic acid). Appl Microbiol Biotechnol. May 2000;53(5):545-52.

Liu et al., Microbial production of R-3-hydroxybutyric acid by recombinant *E. coli* harboring genes of phbA, phbB, and tesB. Appl Microbiol Biotechnol. Sep. 2007;76(4):811-8. Epub Jul. 4, 2007.

Naggert et al., Cloning, sequencing, and characterization of *Escherichia coli* thioesterase II. J Biol Chem. Jun. 15, 1991;266(17):11044-50.

Nuñez et al., Biochemical characterization of the 2-ketoacid reductases encoded by ycdW and yiaE genes in *Escherichia coli*. Biochem J. Mar. 15, 2001;354(Pt 3):707-15.

Park et al., Preparation of optically active β-amino acids from microbial polyester polyhydroxyalkanoates. J Chem Res. Nov. 1, 2001;2001(11):498-9.

Peoples et al., Poly-beta-hydroxybutyrate biosynthesis in *Alcaligenes eutrophus* H16 Characterization of the genes encoding beta-ketothiolase and acetoacetyl-CoA reductase. J Biol Chem. Sep. 15, 1989;264(26):15293-7.

Schubert et al., Cloning of the *Alcaligenes eutrophus* genes for synthesis of poly-beta-hydroxybutyric acid (PHB) and synthesis of PHB in *Escherichia coli* J Bacteriol. Dec. 1988;170(12):5837-47.

Schweiger et al., On the dehydration of (R)-lactate in the fermentation of alanine to propionate by *Clostridium propionicum*. FEBS Lett. Jun. 4, 1984;171(1):79-84.

Seebach et al., From the biopolymer PHB to biological investigations of unnatural β- and γ-peptides. Chimia. 2001;55:345-53.

Slater et al., Multiple beta-ketothiolases mediate poly(beta-hydroxyalkanoate) copolymer synthesis in *Ralstonia eutropha*. J Bacteriol. Apr. 1998;180(8):1979-87.

Stim-Herndon et al., Characterization of an acetyl-CoA C-acetyltransferase (thiolase) gene from *Clostridium acetobutylicum* ATCC 824. Gene. Feb. 27, 1995;154(1):81-5.

Tseng et al., Metabolic engineering of *Escherichia coli* for enhanced production of (R)- and (S)-3-hydroxybutyrate. Appl Environ Microbiol. May 2009;75(10):3137-45. Epub Mar. 20, 2009.

Wang et al., Direct Conversion of (S)-3-Hydroxy-gamma-butyrolactone to Chiral Three-Carbon Building Blocks. J Org Chem. Feb. 5, 1999;64(3):1036-1038.

Wang et al., Synthetic routes to l-carnitine and l-gamma-amino-beta-hydroxybutyric acid from (S)-3-hydroxybutyrolactone by functional group priority switching. Tetrahedron: Asymmetry. May 21, 1999;10(10):1895-901.

Werpy et al., Top value added chemicals from biomass, vol. 1: results of screening for potential candidates from sugars and synthesis gas. Department of Energy, Oak Ridge, TN. Aug. 2004.

Yang et al., Biosynthesis of polylactic acid and its copolymers using evolved propionate CoA transferase and PHA synthase. Biotechnol Bioeng. Jan. 1, 2010;105(1):150-60.

Yasohara et al., Molecular cloning and overexpression of the gene encoding an NADPH-dependent carbonyl reductase from *Candida magnoliae*, involved in stereoselective reduction of ethyl 4-chloro3-3oxobutanoate. Biosci Biotechnol Biochem. Jul. 2000;64(7):1430-6.

* cited by examiner

Figure 4
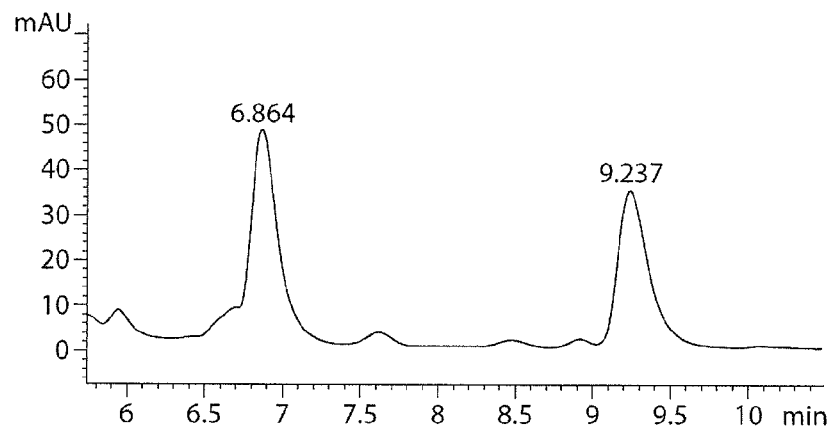
Fig. 4A
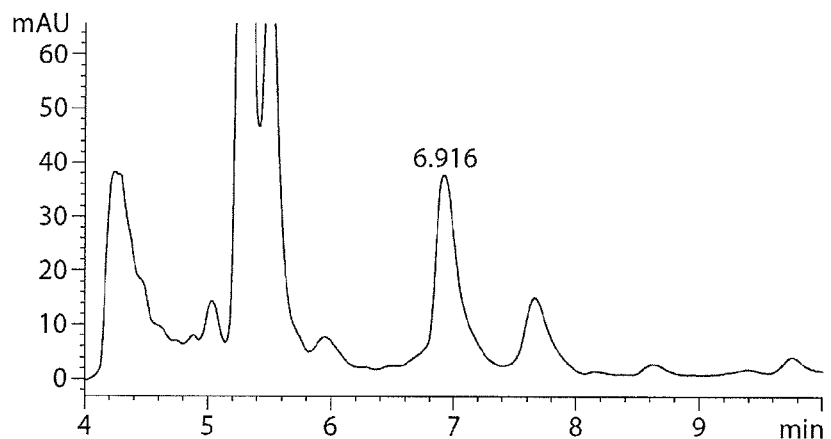
Fig. 4B
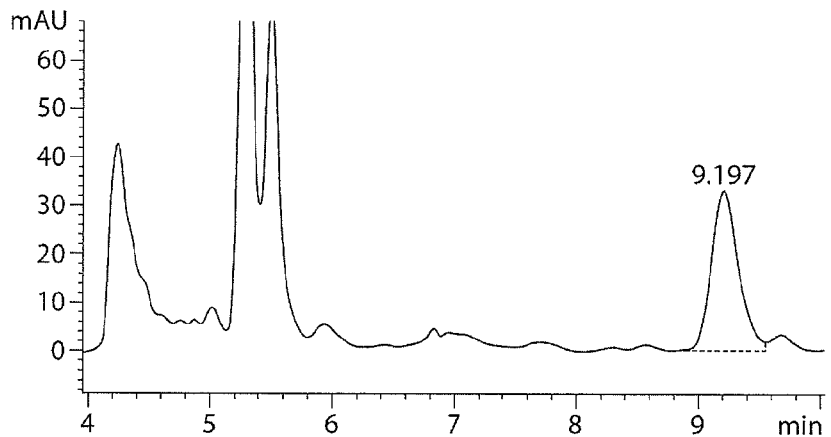
Fig. 4C

A = DHBA Standard
B = phaA-phaB-tesB-pct BL21(DE3) *E. coli* with Glycolate
C = bktB-S1-tesB-pct BL21(DE3) *E. coli* with Glycolate ("Negative Control")

A = 3-HBL + DHBA Standard
B = phaA-phaB-tesB-pct BL21(DE3) *E. coli* with Glycolate
C = bktB-S1-tesB-pct BL21(DE3) *E. coli* with Glycolate ("Negative Control")

```
                         SEQUENCE LISTING

<160> NUMBER OF SEQ ID NOS: 15

<210> SEQ ID NO 1
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 1
gacaccatgg gcatgactga cgttgtcatc gtatc                              35

<210> SEQ ID NO 2
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 2
gacagaattc ttatttgcgc tcgactgc                                      28

<210> SEQ ID NO 3
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 3
gacacatatg actcagcgca ttgc                                          24

<210> SEQ ID NO 4
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 4
gacactcgag tcagcccatg tgcagg                                        26

<210> SEQ ID NO 5
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 5
gacacatatg agtcaggcgc taaaaaaat                                     29

<210> SEQ ID NO 6
<211> LENGTH: 33
<212> TYPE: DNA
```

```
<213> ORGANISM: Artificial Sequence
<220> FEATURE:
<223> OTHER INFORMATION: synthetic oligonucleotide

<400> SEQUENCE: 6
gacactcgag ttaattgtga attacgcatc acc                                 33

<210> SEQ ID NO 7
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 7
gacagaattc atgagaaaag tagaaatcat tacagctg                            38

<210> SEQ ID NO 8
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 8
gacactgcag ttatttttc agtcccatgg g                                    31

<210> SEQ ID NO 9
<211> LENGTH: 1552
<212> TYPE: DNA
<213> ORGANISM: Megasphaera elsdenii

<400> SEQUENCE: 9
atgagaaaag tagaaatcat tacagctgaa caagcagctc agctcgtaaa agacaacgac    60
acgattacgt ctatcggctt tgtcagcagc gcccatccgg aagcactgac caaagctttg   120
gaaaaacggt tcctggacac gaacaccccg cagaacttga cctacatcta tgcaggctct   180
cagggcaaac gcgatggccg tgccgctgaa catctggcac acacaggcct tttgaaacgc   240
gccatcatcg gtcactggca gactgtaccg gctatcggta aactggctgt cgaaaacaag   300
attgaagctt acaacttctc gcagggcacg ttggtccact ggttccgcgc cttggcaggt   360
cataagctcg gcgtcttcac cgacatcggt ctggaaactt cctcgatcc ccgtcagctc   420 ggcggcaagc tcaatgacgt aaccaaagaa gacctcgtca actgatcga agtcgatggt   480 catgaacagc ttttctaccc gaccttcccg gtcaactag ctttcctccg cggtacgtat   540
gctgatgaat ccggcaatat caccatggac gaagaaatcg ggcctttcga agcacttcc   600 gtagcccagg ccgttcacaa ctgtggcggt aaagtcgtcg tccaggtcaa agacgtcgtc   660
gctcacggca gcctcgaccc gcgcatggtc aagatccctg gcatctatgt cgactacgtc   720
gtcgtagcag ctccggaaga ccatcagcag acgtatgact gcgaatacga tccgtccctc   780
agcggtgaac atcgtgctcc tgaaggcgct accgatgcag ctctccccat gagcgctaag   840
aaaatcatcg gccgccgcgg cgctttggaa ttgactgaaa acgctgtcgt caacctcggc   900
gtcggtgctc cggaatacgt tgcttctgtt gccggtgaag aaggtatcgc cgataccatt   960
accctgaccg tcgaaggtgg cgccatcggt ggcgtaccgc agggcggtgc ccgcttcggt  1020
tcgtcccgca atgccgatgc catcatcgac cacacctatc agttcgactt ctacgatggc  1080
ggcggtctgg acatcgctta cctcggcctg gcccagtgcg atggctcggg caacatcaac  1140
gtcagcaagt tcggtactaa cgttgccggc tgcggcggtt tccccaacat ttcccagcag  1200
```

-continued

```
acaccgaatg tttacttctg cggcaccttc acggctggcg gcttgaaaat cgctgtcgaa    1260
gacggcaaag tcaagatcct ccaggaaggc aaagccaaga agttcatcaa agctgtcgac    1320
cagatcactt tcaacggttc ctatgcagcc cgcaacggca aacacgttct ctacatcaca    1380
gaacgctgcg tatttgaact gaccaaagaa ggcttgaaac tcatcgaagt cgcaccgggc    1440
atcgatattg aaaagatat cctcgctcac atggacttca gccgatcat tgataatccg     1500 aaactcatgg atgcccgcct cttccaggac ggtcccatgg gactgaaaaa at           1552
```

```
<210> SEQ ID NO 10
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 10
gacaccatgg gcatgacgcg tgaagtggta g                                    31

<210> SEQ ID NO 11
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 11
gacagaattc tcagatacgc tcgaagatgg                                      30

<210> SEQ ID NO 12
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 12
tatccatatg aaaaaggtat gtgttatagg tgc                                  33

<210> SEQ ID NO 13
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 13
gacactcgag ttattttgaa taatcgtaga aaccttttc                            39

<210> SEQ ID NO 14
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 14
gacaccatgg gcatgagaga tgtagtaata gtaagtgctg taaga                     45

<210> SEQ ID NO 15
<211> LENGTH: 37
<212> TYPE: DNA
<213> ORGANISM: Artificial Sequence
<220> FEATURE:
<223> OTHER INFORMATION: synthetic oligonucleotide
```

```
<400> SEQUENCE: 15
gacagaattc tatttagtct ctttcaacta cgagagc                                    37
```

MICROBIAL PRODUCTION OF 3-HYDROXYACIDS FROM GLUCOSE AND GLYCOLATE

RELATED APPLICATIONS

This application claims the benefit under 35 U.S.C. §119 (e) of U.S. provisional application Ser. No. 61/158,216, filed on Mar. 6, 2009, the disclosure of which is incorporated by reference herein in its entirety.

GOVERNMENT INTEREST

This invention was made with Government support under Grant No. EEC0540879 awarded by the National Science Foundation. The government has certain rights in this invention.

FIELD OF THE INVENTION

The invention relates to the production of 3-hydroxyacids such as 3,4-dihydroxybutyrate and 3-hydroxybutyrolactone through recombinant gene expression.

BACKGROUND OF INVENTION 3,4-dihydroxybutyrate (DHBA) and 3-hydroxybutyrolactone (3-HBL) are highly useful chiral intermediates that can be used to synthesize statin-class drugs like CRESTOR® and LIPITOR®, carnitine, and other fine chemicals. The annual market for statin drugs was estimated to be $10-15 billion in 2003 and 2004, while the annual demand for carnitine (which is used as a vitamin supplement) is estimated to be several hundred metric tons. DHBA and 3-HBL can also be readily derivatized into valuable compounds like carnitine, which has an approximate $5 per gram cost and is used as a vitamin and nutritional supplement.

Currently DHBA is not commercially available, while 3-HBL costs $30-100 per gram. The high cost and low availability of these compounds increases the costs of statin drugs. Existing methods for the synthesis of DHBA and 3-HBL rely on crude, harsh chemical synthetic means, such as the harsh reduction of malic acid or the breakdown of various hexose sugars with acid. Such chemical synthetic methods produce several byproducts, necessitating the extensive purification of the DHBA or 3-HBL product. These drawbacks make chemical synthesis of DHBA and 3-HBL relatively unattractive and uneconomical.

SUMMARY OF INVENTION

Described herein are efficient biological methods for producing 3-hydroxyacids such as 3,4-dihydroxybutyrate (DHBA) and 3-hydroxybutyrolactone (3-HBL) in cells such as *E. coli* cells. The methods include use of cells that recombinantly express (1) a pct gene, (2) at least one of a phaA, thiL, atoB or bktB gene, and (3) at least one of a phaB, S1 or hbd gene, and optionally recombinant expression of the tesB gene and/or a gene encoding for glycolate reductase, as an efficient and cost-effective means of synthesizing DHBA and 3-HBL.

Aspects of the invention relate to a cell that recombinantly expresses (1) a pct gene, (2) at least one of a phaA, thiL, atoB or bktB gene, and (3) at least one of a phaB or hbd gene. In some embodiments the cell further recombinantly expresses a tesB gene and/or a gene encoding for glycolate reductase. The cell can be a bacterial cell, a fungal cell (including a yeast cell), a plant cell, an insect cell or an animal cell. In some embodiments the cell is a bacterial cell such as an *Escherichia coli* cell.

Alternatively, it should be appreciated that not all of the genes need to be recombinantly expressed in the cells associated with methods of the invention. In embodiments where one or more of the genes associated with the invention are expressed endogenously in a cell, then the cell would not necessarily require recombinant expression of the same one or more genes that are endogenously expressed in the cell. In these embodiments, the cell may be supplemented with recombinant expression of whichever genes in the pathway are not endogenously expressed in the cell.

In some embodiments, one or more of the pct, phaA, thiL, atoB, bktB, phaB, hbd, tesB and glycolate reductase gene(s) is expressed from one or more plasmid(s). In some embodiments one or more of the pct, phaA, thiL, atoB, bktB, phaB, hbd, tesB and glycolate reductase gene(s) is integrated into the genome of the cell. In certain embodiments the phaA, bktB and/or phaB gene(s) is a *Ralstonia eutropha* gene, such as a *Ralstonia eutropha* H16 gene. In certain embodiments, the pct gene is a *Megasphaera elsdenii* gene, such as a *Megasphaera elsdenii* BE2-2083 gene. In certain embodiments the tesB gene is an *Escherichia coli* gene, such as an *Escherichia coli* K12 gene. In some embodiments the gene encoding for glycolate reductase is a *Pseudomonas* gene or a *Saccharomyces* gene.

Aspects of the invention relate to methods for producing DHBA and/or 3-HBL, the method including culturing a cell associated with the invention to produce DHBA and/or 3-HBL, and optionally recovering the DHBA and/or 3-HBL from the cells. In some embodiments the cell is cultured in the presence of glucose and/or glycolate and/or propionate.

Aspects of the invention relate to methods for producing a cell that has increased DHBA and/or 3-HBL production comprising recombinantly expressing (1) a pct gene, (2) at least one of a phaA, thiL, atoB or bktB gene, and (3) at least one of a phaB or hbd gene in the cell. In some embodiments the cell further recombinantly expresses a tesB gene and/or a gene encoding for glycolate reductase. In some embodiments the cell is provided with glucose and/or glycolate and/or propionate. The cell can be a bacterial cell, a fungal cell (including a yeast cell), a plant cell, an insect cell or an animal cell. In some embodiments the cell is a bacterial cell such as an *Escherichia coli* cell. In some embodiments, the cell expresses recA and/or endA. In certain embodiments, the cell is an *E. coli* MG1655(DE3) cell.

In some embodiments, one or more of the pct, phaA, thiL, atoB, bktB, phaB, hbd, tesB and glycolate reductase gene(s) is expressed from one or more plasmid(s). In some embodiments one or more of the pct, phaA, thiL, atoB, bktB, phaB, hbd, tesB and glycolate reductase gene(s) is integrated into the genome of the cell. In certain embodiments the phaA, bktB and/or phaB gene(s) is a *Ralstonia eutropha* gene, such as a *Ralstonia eutropha* H16 gene. In certain embodiments, the pct gene is a *Megasphaera elsdenii* gene, such as a *Megasphaera elsdenii* BE2-2083 gene. In certain embodiments the tesB gene is an *Escherichia coli* gene, such as an *Escherichia coli* K12 gene. In some embodiments the gene encoding for glycolate reductase is a *Pseudomonas* gene or a *Saccharomyces* gene.

Aspects of the invention relate to DHBA produced by a cell culture wherein the cells within the cell culture have been genetically modified to recombinantly express (1) a pct gene, (2) at least one of a phaA, thiL, atoB or bktB gene, and (3) at least one of a phaB or hbd gene. In some embodiments, the cell further recombinantly expresses a tesB gene and/or glycolate reductase. In some embodiments the cell is provided with glucose and/or glycolate. The cell can be a bacterial cell, a fungal cell (including a yeast cell), a plant cell, an insect cell or an animal cell. In some embodiments the cell is a bacterial cell such as an *Escherichia coli* cell.

In some embodiments, one or more of the pct, phaA, thil, atoB, bktB, phaB, hbd, tesB and glycolate reductase gene(s) is expressed from one or more plasmid(s). In some embodiments one or more of the pct, phaA, thil, atoB, bktB, phaB, hbd, tesB and glycolate reductase gene(s) is integrated into the genome of the cell. In certain embodiments the phaA, bktB and/or phaB gene(s) is a *Ralstonia eutropha* gene, such as a *Ralstonia eutropha* H16 gene. In certain embodiments, the pct gene is a *Megasphaera elsdenii* gene, such as a *Megasphaera elsdenii* BE2-2083 gene. In certain embodiments the tesB gene is an *Escherichia coli* gene, such as an *Escherichia coli* K12 gene. In some embodiments the gene encoding for glycolate reductase is a *Pseudomonas* gene or a *Saccharomyces* gene.

Aspects of the invention relate to 3-HBL produced by a cell culture wherein the cells within the cell culture have been genetically modified to recombinantly express (1) a pct gene, (2) at least one of a phaA, thil, atoB or bktB gene, and (3) at least one of a phaB or hbd gene. In some embodiments, the cell further recombinantly expresses a tesB gene and/or glycolate reductase. In some embodiments the cell is provided with glucose and/or glycolate. The cell can be a bacterial cell, a fungal cell (including a yeast cell), a plant cell, an insect cell or an animal cell. In some embodiments the cell is a bacterial cell such as an *Escherichia coli* cell.

In some embodiments, one or more of the pct, phaA, thil, atoB, bktB, phaB, hbd, tesB and glycolate reductase gene(s) is expressed from one or more plasmid(s). In some embodiments one or more of the pct, phaA, thil, atoB, bktB, phaB, hbd, tesB and glycolate reductase gene(s) is integrated into the genome of the cell. In certain embodiments the phaA, bktB and/or phaB gene(s) is a *Ralstonia eutropha* gene, such as a *Ralstonia eutropha* H16 gene. In certain embodiments, the pct gene is a *Megasphaera elsdenii* gene, such as a *Megasphaera elsdenii* BE2-2083 gene. In certain embodiments the tesB gene is an *Escherichia coli* gene, such as an *Escherichia coli* K12 gene. In some embodiments the gene encoding for glycolate reductase is a *Pseudomonas* gene or a *Saccharomyces* gene.

In some embodiments, a cell that expresses a recombinant pathway described herein also expresses recA and/or endA. In certain embodiments, the cell is an *E. coli* MG1655(DE3) cell. In some embodiments, supernatants from cell cultures of recombinant cells described herein are subjected to lactonization.

Aspects of the invention relate to cell cultures produced by culturing any of the cells associated with the invention. In some embodiments, the cell culture contains at least 200 mg $L^{-1}$ DHBA. In certain embodiments, the cell culture contains at least 1 g $L^{-1}$ DHBA. In some embodiments, the cell culture contains at least 10 mg $L^{-1}$ 3-HBL. In certain embodiments, the cell culture contains at least 100 mg $L^{-1}$, or at least 500 mg $L^{-1}$ of 3-HBL.

Aspects of the invention relate to supernatant of cell cultures produced by culturing any of the cells associated with the invention. In some embodiments, the supernatant contains at least 200 mg $L^{-1}$ DHBA. In certain embodiments, the supernatant contains at least 1 g $L^{-1}$ DHBA. In some embodiments, the supernatant contains at least 10 mg $L^{-1}$ 3-HBL. In certain embodiments, the supernatant contains at least 100 mg $L^{-1}$ or at least 500 mg of 3-HBL. In some embodiments, the supernatant is subject to lactonization. In certain embodiments, lactonization is achieved through acidification to reduce the pH of the supernatant. In some embodiments, lactonization is achieved through auto-lactonization of DHBA-CoA.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 4 depicts HPLC spectra of methyl esters of 3HV. FIG. 4A represents a racemic 3HV standard with the two stereoisomers eluting at 6.9 and 9.2 min; FIG. 4B is culture medium from *E. coli* expressing ptb-buk, phaB, and bktB with a peak at 6.9 min; and FIG. 4C is culture medium from *E. coli* expressing ptb-buk, hbd, bktB, and tesB with a peak at 9.2 min. The ptb-buk operon encodes a phosphotransbutyrase (ptb) and a butyrokinase (buk) from *Clostridium acetobutylicum* that functions to produce high levels of propionyl-CoA from propionate, similar to pct. All samples were boiled in acidic methanol to form methyl-3HV esters prior to HPLC analysis. Chiral 3HB experiments using this same chiral HPLC analysis protocol strongly suggests that the 6.9 and 9.2 min peaks represent (R)-3HV and (S)-3HV respectively.

DETAILED DESCRIPTION

Figure 1:
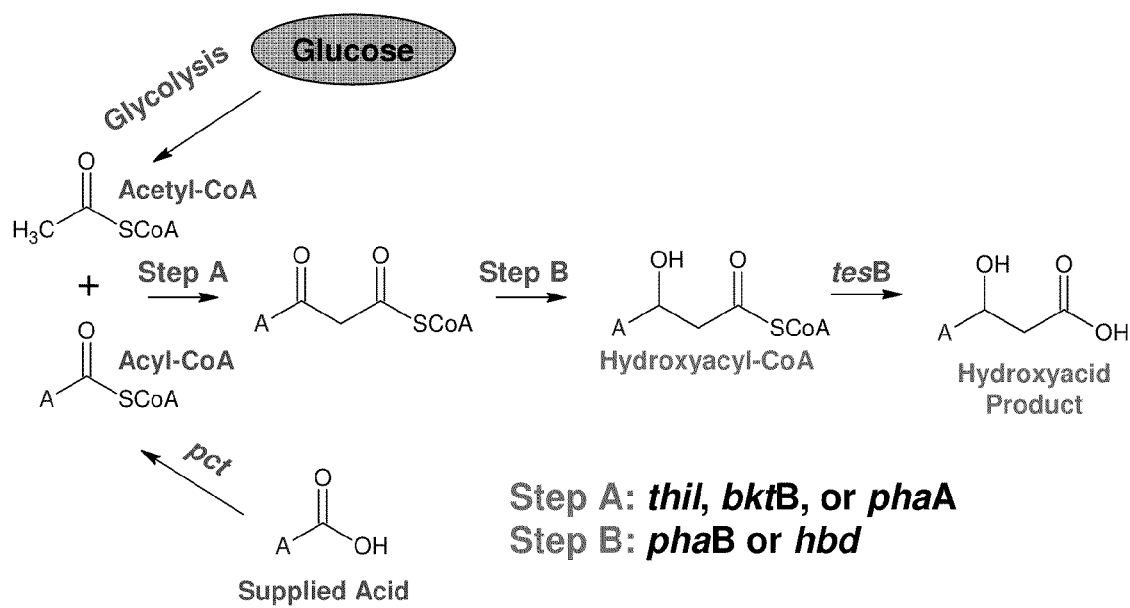
FIG. 1 is a schematic depicting the 3-hydroxyalkanoic acid pathway. The presence of pct generates acyl-CoA molecules used in the condensation reaction with acetyl-CoA.
Figure 2:
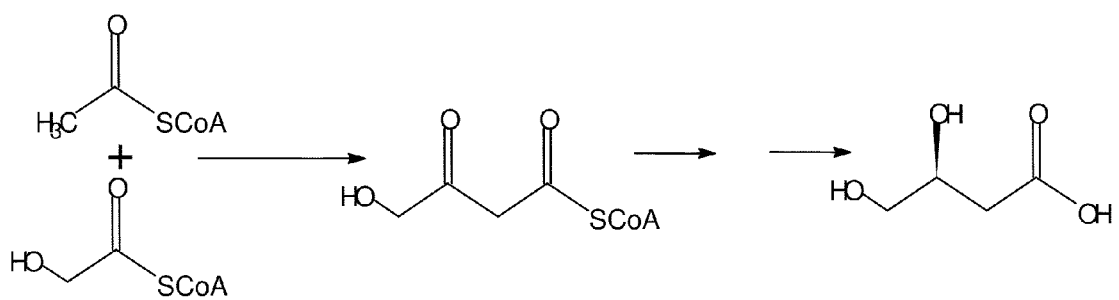
FIG. 2 is a schematic depicting an adaptation to the 3-hydroxyalkanoic acid pathway utilized herein for synthesizing DHBA.

Previous methods for the synthesis of DHBA and 3-HBL have relied on crude, harsh chemical synthetic means, while biological production of DHBA and 3-HBL has not been considered an option. In fact, while 3-HBL has been listed in a recent report from the Department of Energy as a top ten value-added chemical from biomass (Werpy and Petersen, 2004), this report also claimed that a biological route for 3-HBL synthesis was "not likely" and instead called for the development of better chemical synthetic processes for 3-HBL. Described herein is the surprising discovery that DHBA and 3-HBL can be produced through a biological process involving recombinant gene expression in cells. Methods and compositions of the invention relate to the production of DHBA and 3-HBL in a cell that recombinantly expresses one or more genes including pct, phaA, thil, atoB, bktB, phaB, Sl, hbd and tesB. This system represents an efficient new method for producing DHBA and 3-HBL, molecules that have a wide variety of applications.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The 3-hydroxyalkanoic Acid Pathway

Methods and compositions described herein use the 3-hydroxyalkanoic acid pathway to synthesize 3-hydroxyacids such as 3-hydroxybutyrolactone (3-HBL) and/or its hydrolyzed form 3,4-dihydroxybutyric acid (DHBA) from sugars and sugar-derived substrates. As used herein, a "hydroxyacid" refers to a compound that contains both a carboxyl and a hydroxyl moiety.

FIG. 1 presents a schematic of the 3-hydroxyalkanoic acid pathway. In methods and compositions associated with the invention, one or more acetoacetyl-CoA thiolases (such as thil, bktB, phaA or atoB) is used to perform a condensation reaction to yield a 3-ketoacyl-CoA intermediate, which is subsequently reduced by either phaB or hbd to yield a 3-hydroxyacyl-CoA compound. Optionally, the CoA moiety from the 3-hydroxyacyl-CoA compound can be hydrolyzed by tesB, liberating the free 3-hydroxyacid.

Short chain acyl-CoA compounds that would be candidate substrates for this pathway are not readily available metabolites in *E. coli*. To circumvent this, propionyl-CoA transferase (pct), an enzyme with broad substrate-specificity, is used to exchange CoA moieties between short-chain organic acids. In methods and compositions described herein, pct is used to transfer CoA from acetyl-CoA to a substrate such as an acid supplied to the cell, forming the acyl-CoA for use by the pathway. In some embodiments, a phosphotransbutyrase (ptb) gene and a butyrokinase (buk) gene are used to produce propionyl-CoA instead of pct.

In some embodiments, the substrate is propionate, and a product produced by the pathway is 3-hydroxyvalerate (3HV). In other embodiments, the substrate is glycolate and a product produced by the pathway is 3-HBL and/or DHBA. It should be appreciated that other substrates would also be compatible with aspects of the invention, as would be apparent to one or ordinary skill in the art, and that more than one substrate could be used simultaneously. In some embodiments, glucose is also provided. In some embodiments, 3HV and/or DHBA and/or 3-HBL is produced in cultures that express bktB phaB, phaA-phaB, bktB-hbd, or thil-phaB.

Aspects of the invention relate to recombinant expression of one or more genes encoding for one or more enzymes in the 3-hydroxyalkanoic acid pathway. Enzymes associated with this pathway include thiolases (encoded by thil, bktB, phaA or atoB) and reductases (phaB, hbd or Sl). Aspects of the invention also relate to recombinant expression of propionyl-CoA transferase (encoded by pct) and thioesterase B (encoded by tesB). In some embodiments, a cell associated with the invention also recombinantly expresses a gene encoding for glycolate reductase.

According to aspects of the invention, cell(s) that recombinantly express one or more genes associated with the invention, and the use of such cells in producing DHBA and 3-HBL are provided. It should be appreciated that the genes associated with the invention can be obtained from a variety of sources. In some embodiments, the phaA, phaB, and bktB genes are obtained from a strain of *Ralstonia eutropha*, such as *Ralstonia eutropha* H16, the tesB gene is obtained from a strain of *Escherichia coli* such as *Escherichia coli* K12, the pct gene is obtained from a strain of *Megasphaera elsdenii*, such as *Megasphaera elsdenii* BE2-2083, the atoB gene is obtained from a strain of *P. putida*, such as *P. putida* KT2440, the hbd and thil genes are obtained from a strain of *Clostridium acetobutylicum*, such as *C. acetobutylicum* 824, and the S1 gene is obtained from a strain of *C. magnolia*. In some embodiments, wherein ptb and buk are expressed instead of pct, the ptb and buk genes are coexpressed on an operon. In some embodiments, the ptb-buk operon is obtained from a strain of *Clostridium acetobutylicum*. In some embodiments, the sequence of the phaA gene is represented by GenBank accession no. P14611 (Peoples and Sinskey, 1989), the sequence of the phaB gene is represented by GenBank accession no. P14697 (Peoples and Sinskey, 1989), the sequence of the tesB gene is represented by Genbank accession no. P23911 or ABC97996 (Naggert et al., 1991) and the sequence of the pct gene is represented by the sequence depicted in SEQ ID NO:9 (Taguchi et al., 2008). In some embodiments, the sequence of the ptb gene is represented by Genbank accession no. AAK81016. In some embodiments, the sequence of the buk gene is represented by Genbank accession no. AAK81015. It should be appreciated that any of the nucleic acids and/or polypeptides described herein can be codon-optimized and expressed recombinantly in a codon-optimized form.

As one of ordinary skill in the art would be aware, homologous genes for these enzymes could be obtained from other species and could be identified by homology searches, for example through a protein BLAST search, available at the National Center for Biotechnology Information (NCBI) internet site (ncbi.nlm.nih.gov). Genes associated with the invention can be PCR amplified from DNA from any source of DNA which contains the given gene. In some embodiments, genes associated with the invention are synthetic. Any means of obtaining a gene encoding the enzymes associated with the invention are compatible with the instant invention.

The invention thus involves recombinant expression of genes encoding enzymes discussed above, functional modifications and variants of the foregoing, as well as uses relating thereto. Homologs and alleles of the nucleic acids associated with the invention can be identified by conventional techniques. Also encompassed by the invention are nucleic acids that hybridize under stringent conditions to the nucleic acids described herein. The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$(pH7), 0.5% SDS, 2 mM EDTA). SSC is 0.15M sodium chloride/0.015M sodium citrate, pH7; SDS is sodium dodecyl sulphate; and EDTA is ethylenediaminetetracetic acid. After hybridization, the membrane upon which the DNA is transferred is washed, for example, in 2×SSC at room temperature and then at 0.1-0.5×SSC/0.1×SDS at temperatures up to 68° C.

There are other conditions, reagents, and so forth which can be used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of nucleic acids of the invention (e.g., by using lower stringency conditions). The skilled artisan also is familiar with the methodology for screening cells and libraries for expression of such molecules which then are routinely isolated, followed by isolation of the pertinent nucleic acid molecule and sequencing.

In general, homologs and alleles typically will share at least 75% nucleotide identity and/or at least 90% amino acid identity to the sequences of nucleic acids and polypeptides, respectively, in some instances will share at least 90% nucleotide identity and/or at least 95% amino acid identity and in still other instances will share at least 95% nucleotide identity and/or at least 99% amino acid identity. The homology can be calculated using various, publicly available software tools developed by NCBI (Bethesda, Maryland) that can be obtained through the NCBI internet site. Exemplary tools include the BLAST software, also available at the NCBI internet site (www.ncbi.nlm.nih.gov). Pairwise and ClustalW alignments (BLOSUM30 matrix setting) as well as Kyte-Doolittle hydropathic analysis can be obtained using the MacVector sequence analysis software (Oxford Molecular Group). Watson-Crick complements of the foregoing nucleic acids also are embraced by the invention.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code. The invention also embraces codon optimization to suit optimal codon usage of a host cell.

The invention also provides modified nucleic acid molecules which include additions, substitutions and deletions of one or more nucleotides. In preferred embodiments, these modified nucleic acid molecules and/or the polypeptides they encode retain at least one activity or function of the unmodified nucleic acid molecule and/or the polypeptides, such as enzymatic activity. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art.

For example, modified nucleic acid molecules which encode polypeptides having single amino acid changes can be prepared. Each of these nucleic acid molecules can have one, two or three nucleotide substitutions exclusive of nucleotide changes corresponding to the degeneracy of the genetic code as described herein. Likewise, modified nucleic acid molecules which encode polypeptides having two amino acid changes can be prepared which have, e.g., 2-6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions which code for the amino acid substitutions. Additional nucleic acid molecules that encode polypeptides having additional substitutions (i.e., 3 or more), additions or deletions (e.g., by introduction of a stop codon or a splice site(s)) also can be prepared and are embraced by the invention as readily envisioned by one of ordinary skill in the art. Any of the foregoing nucleic acids or polypeptides can be tested by routine experimentation for retention of structural relation or activity to the nucleic acids and/or polypeptides disclosed herein.

The invention embraces variants of polypeptides. As used herein, a "variant" of a polypeptide is a polypeptide which contains one or more modifications to the primary amino acid sequence of the polypeptide. Modifications which create a variant can be made to a polypeptide 1) to reduce or eliminate an activity of a polypeptide; 2) to enhance a property of a polypeptide; 3) to provide a novel activity or property to a polypeptide, such as addition of an antigenic epitope or addition of a detectable moiety; or 4) to provide equivalent or better binding between molecules (e.g., an enzymatic substrate). Modifications to a polypeptide are typically made to the nucleic acid which encodes the polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the amino acid sequence. One of skill in the art will be familiar with methods for predicting the effect on protein conformation of a change in protein sequence, and can thus "design" a variant of a polypeptide according to known methods. One example of such a method is described by Dahiyat and Mayo in *Science* 278:82-87, 1997, whereby proteins can be designed de novo. The method can be applied to a known protein to vary a only a portion of the polypeptide sequence. By applying the computational methods of Dahiyat and Mayo, specific variants of a polypeptide can be proposed and tested to determine whether the variant retains a desired conformation.

In general, variants include polypeptides which are modified specifically to alter a feature of the polypeptide unrelated to its desired physiological activity. For example, cysteine residues can be substituted or deleted to prevent unwanted disulfide linkages. Similarly, certain amino acids can be changed to enhance expression of a polypeptide by eliminating proteolysis by proteases in an expression system (e.g., dibasic amino acid residues in yeast expression systems in which KEX2 protease activity is present).

Mutations of a nucleic acid which encode a polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a gene or cDNA clone to enhance expression of the polypeptide. The activity of variant polypeptides can be tested by cloning the gene encoding the variant polypeptide into a bacterial or mammalian expression vector, introducing the vector into an appropriate host cell, expressing the variant polypeptide, and testing for a functional capability of the polypeptides as disclosed herein.

The skilled artisan will also realize that conservative amino acid substitutions may be made in polypeptides to provide functionally equivalent variants of the foregoing polypeptides, i.e., the variants retain the functional capabilities of the polypeptides. As used herein, a "conservative amino acid substitution" refers to an amino acid substitution which does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants of polypeptides include conservative amino acid substitutions in the amino acid sequences of proteins disclosed herein. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In general, it is preferred that fewer than all of the amino acids are changed when preparing variant polypeptides. Where particular amino acid residues are known to confer function, such amino acids will not be replaced, or alternatively, will be replaced by conservative amino acid substitutions. Preferably, 1, 2, 3, 4, 5, 6, 7, 8, 9, 10, 11, 12, 13, 14, 15, 16, 17, 18, 19, 20 residues can be changed when preparing variant polypeptides. It is generally preferred that the fewest number of substitutions is made. Thus, one method for generating variant polypeptides is to substitute all other amino acids for a particular single amino acid, then assay activity of the variant, then repeat the process with one or more of the polypeptides having the best activity.

Conservative amino-acid substitutions in the amino acid sequence of a polypeptide to produce functionally equivalent variants of the polypeptide typically are made by alteration of a nucleic acid encoding the polypeptide. Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488-492, 1985), or by chemical synthesis of a gene encoding a polypeptide.

The invention encompasses any type of cell that recombinantly expresses genes associated with the invention, including prokaryotic and eukaryotic cells. In some embodiments the cell is a bacterial cell, such as *Escherichia* spp., *Streptomyces* spp., *Zymonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp. and *Pantoea* spp. The bacterial cell can be a Gram-negative cell such as an *Escherichia coli* (*E. coli*) cell, or a Gram-positive cell such as a species of *Bacillus*. In other embodiments the cell is a fungal cell such as yeast cells, e.g., *Saccharomyces* spp., *Schizosaccharomyces* spp., *Pichia* spp., *Paffia* spp., *Kluyveromyces* spp., *Candida* spp., *Talaromyces* spp., *Brettanomyces* spp., *Pachysolen* spp., *Debaryomyces* spp., *Yarrowia* spp. and industrial polyploid yeast strains. Preferably the yeast strain is a *S. cerevisiae* strain. Other examples of fungi include *Aspergillus* spp., *Pennicilium* spp., *Fusarium* spp., *Rhizopus* spp., *Acremonium* spp., *Neurospora* spp., *Sordaria* spp., *Magnaporthe* spp., *Allomyces* spp., *Ustilago* spp., *Botrytis* spp., and *Trichoderma* spp. In other embodiments the cell is an algal cell, a plant cell, or a mammalian cell. It should be appreciated that some cells compatible with the invention may express an endogenous copy of one or more of the genes associated with the invention as well as a recombinant copy. In some embodiments if a cell has an endogenous copy of one or more of the genes associated with the invention then the methods will not necessarily require adding a recombinant copy of the gene(s) that are endogenously expressed. In some embodiments the cell may endogenously express one or more enzymes from the pathways described herein and may recombinantly express one or more other enzymes from the pathways described herein for efficient production of DHBA and/or 3-HBL.

In some embodiments, one or more of the genes associated with the invention is expressed in a recombinant expression vector. As used herein, a "vector" may be any of a number of nucleic acids into which a desired sequence or sequences may be inserted by restriction and ligation for transport between different genetic environments or for expression in a host cell. Vectors are typically composed of DNA although RNA vectors are also available. Vectors include, but are not limited to: plasmids, fosmids, phagemids, virus genomes and artificial chromosomes.

A cloning vector is one which is able to replicate autonomously or integrated in the genome in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host cell such as a host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript can be translated into the desired protein or polypeptide.

When the nucleic acid molecule that encodes any of the enzymes of the claimed invention is expressed in a cell, a variety of transcription control sequences (e.g., promoter/enhancer sequences) can be used to direct its expression. The promoter can be a native promoter, i.e., the promoter of the gene in its endogenous context, which provides normal regulation of expression of the gene. In some embodiments the promoter can be constitutive, i.e., the promoter is unregulated allowing for continual transcription of its associated gene. A variety of conditional promoters also can be used, such as promoters controlled by the presence or absence of a molecule.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual, Second Edition*, Cold Spring Harbor Laboratory Press, 1989. Cells are genetically engineered by the introduction into the cells of heterologous DNA (RNA). That heterologous DNA (RNA) is placed under operable control of transcriptional elements to permit the expression of the heterologous DNA in the host cell. Heterologous expression of genes associated with the invention, for production of DHBA and 3-HBL, is demonstrated in the Examples section using *E. coli*. The novel method for producing DHBA and 3-HBL can also be expressed in other bacterial cells, archaeal cells, fungi (including yeast cells), mammalian cells, plant cells, etc.

A nucleic acid molecule that encodes the enzyme of the claimed invention can be introduced into a cell or cells using methods and techniques that are standard in the art. For example, nucleic acid molecules can be introduced by standard protocols such as transformation including chemical transformation and electroporation, transduction, particle bombardment, etc. Expressing the nucleic acid molecule encoding the enzymes of the claimed invention also may be accomplished by integrating the nucleic acid molecule into the genome.

In some embodiments one or more genes associated with the invention is expressed recombinantly in a bacterial cell. Bacterial cells according to the invention can be cultured in media of any type (rich or minimal) and any composition. As would be understood by one of ordinary skill in the art, routine optimization would allow for use of a variety of types of media. The selected medium can be supplemented with various additional components. Some non-limiting examples of supplemental components include glucose, antibiotics, IPTG for gene induction, ATCC Trace Mineral Supplement, glucose, glycolate and propionate. Similarly, other aspects of the medium, and growth conditions of the cells of the invention may be optimized through routine experimentation. For example, pH and temperature are non-limiting examples of factors which can be optimized. In some embodiments, factors such as choice of media, media supplements, and temperature can influence production levels of 3-hydroxyacids such as DHBA and/or 3-HBL. In some embodiments the concentration and amount of a supplemental component may be optimized. In some embodiments, how often the media is supplemented with one or more supplemental components, and the amount of time that the media is cultured before harvesting DHBA and/or 3-HBL is optimized.

In some embodiments the methods associated with the invention, for the production of DHBA and 3-HBL, can be modified to use only glucose rather than glucose and glycolate by the addition of a glycolate reductase gene. This gene, which is found in a variety of organisms such as *Pseudomonas* and *Saccharomyces*, reduces glyoxylate, which can be produced from glucose via the citric acid cycle, to glycolate for use in synthesizing DHBA and 3-HBL.

According to aspects of the invention, high titers of 3HV, DHBA and/or 3-HBL are produced through the recombinant expression of genes associated with the invention, in a cell. As used herein "high titer" refers to a titer in the milligrams per liter (mg $L^{-1}$) scale. The titer produced for a given product will be influenced by multiple factors including choice of media.

In some embodiments, the titer of 3HV is at least 100 mg $L^{-1}$. For example, the titer can be at least approximately 100, 150, 200, 250, 300, 350, 400, 450, 500, 550, 600, 650, 700, 750, 800, 850 or more than 850 mg $L^{-1}$. As demonstrated in the Examples section, in some embodiments, in cultures expressing bktB-phaB, the titer of 3HV is approximately 537 mg $L^{-1}$, in cultures expressing phaA-phaB, the titer of 3HV is approximately 142 mg $L^{-1}$, and in cultures expressing bktB-hbd, the titer of 3HV is approximately 522 mg $L^{-1}$. Without wishing to be bound by any theory, the observation that pathways with bktB yield high 3HV titer is consistent with reports that BktB has high activity towards the condensation of a $C_3$ substrate with a $C_2$ to form a $C_5$ product (Slater et al., 1998). In some embodiments, 3-hydroxyalkanoic acid pathways expressing phaB make a different stereoisomer of 3HV than pathways expressing hbd. In some embodiments, the phaB pathway generates (R)-3HV and the hbd pathway generates (S)-3HV.

In some embodiments the titer of DHBA is at least 25 mg $L^{-1}$ in minimal media. For example the titer may be at least approximately 25, 50, 75, 100, 125, 150, 175, 200, 225, 250, 275, 300 or more than 300 mg $L^{-1}$. In some embodiments the titer for production of DHBA is at least 200 mg $L^{-1}$ in rich media. For example the titer may be at least approximately 200, 225, 250, 275, 300, 325, 350, 375, 400, 425, 450, 475, 500, 525, 550, 575, 600, 625, 650, 675, 700, 750, 775, 800 or 900 mg $L^{-1}$, or 1, 1.5, 2, 2.5, 3, 3.5, 4, 4.5, 5, or more than 5 g $L^{-1}$. In some embodiments the titer for production of 3-HBL is at least 1 mg $L^{-1}$ in minimal media. For example the titer may be at least approximately 1, 2, 3, 4, 5, 6, 7, 8, 9, 10, 15, 20, 25, 30, 35, 40, 45, 50, or more than 50 mg $L^{-1}$. In some embodiments the titer for production of 3-HBL is at least 10 mg $L^{-1}$ in rich media. For example the titer may be at least approximately 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 350, 400, 450, 500, 550, 600, 650, 700, 750, 800, 850 or 900 mg $L^{-1}$, or 1, 1.5, 2, 2.5, 3, 3.5, 4, 4.5, 5 or more than 5 g $L^{-1}$.

As demonstrated in the Examples section, cultures expressing bktB-phaB produced titers of DHBA and 3-HBL of approximately 573±30 mg $L^{-1}$ and 178±4 mg $L^{-1}$ respectively, cultures expressing phaA-phaB produced titers of DHBA and 3-HBL of approximately 492±19 mg $L^{-1}$ and 107±3 mg $L^{-1}$ respectively, and cultures expressing thil-phaB produced titers of DHBA and 3-HBL of approximately 247±57 mg $L^{-1}$ and 96±14 mg $L^{-1}$ respectively. In some embodiments, cultures expressing hbd produce only DHBA. In certain embodiments, in cultures expressing bktB-hbd, DHBA titers are approximately 47±10 mg $L^{-1}$.

The 3-hydroxyalkanoic pathway can be modulated to produce more DHBA or 3-HBL through the presence or absence of the thioesterase TesB. As demonstrated in the Examples section, recombinant expression of tesB leads to production of significantly more DHBA (approximately 573 mg $L^{-1}$ for the bktB-phaB pathway combination) than 3-HBL (approximately 178 mg $L^{-1}$). In some embodiments, without tesB expression, more 3-HBL is made (approximately 270 mg $L^{-1}$ for bktB-phaB) than DHBA (approximately 21 mg $L^{-1}$). In certain embodiments, expression of bktB-phaB-pct yields a 3-HBL titer of approximately 270±3 mg $L^{-1}$. Without wishing to be bound by any theory, the small amount of DHBA formed in the absence of recombinant tesB may be due to the expression of genomic tesB, as this gene is native to *E. coli* (Huisman et al., 1991).

Figure 12:
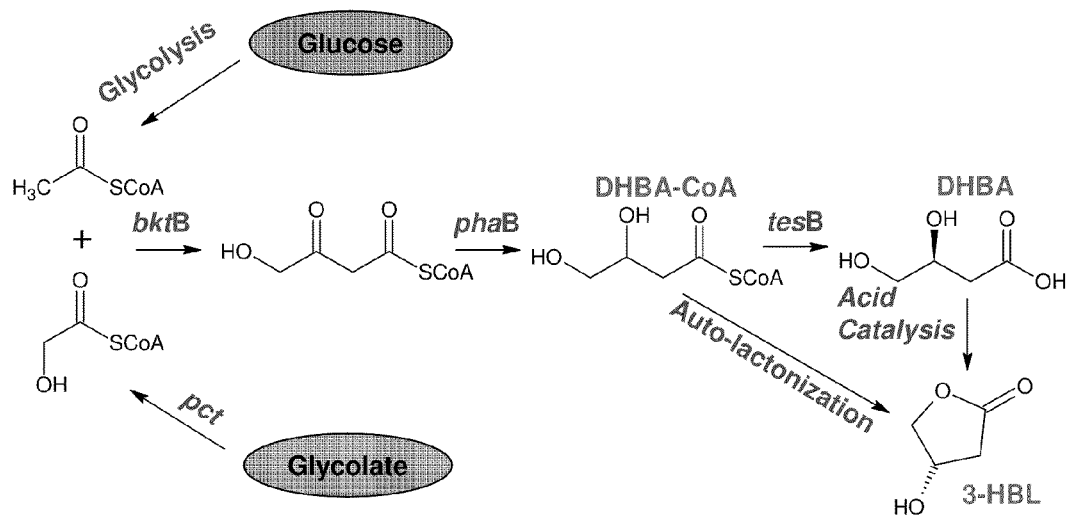
FIG. 12 depicts a 3-Hydroxyalkanoic acid pathway scheme for DHBA and 3-HBL production from glucose and glycolate, highlighting the branch point at DHBA-CoA. With the expression of recombinant tesB, more DHBA is produced by the pathway than 3-HBL (FIG. 8), however in the absence of tesB, more 3-HBL is produced while little DHBA is made, suggesting that DHBA-CoA can self-lactonize into 3-HBL in vivo. Here the pathway is shown with bktB and phaB as the acetoacetyl-CoA thiolase and 3-hydroxybutyryl-CoA reductase, as this pair of genes was shown to yield the highest levels of DHBA and 3-HBL (FIG. 5).

Lactonization can be used to improve titers of 3-HBL. As used herein, lactonization refers to formation of a lactone by intramolecular attack of a hydroxyl group on an activated carbonyl group. Supernatants from cultures that produce more DHBA than 3-HBL can be acidified, such as through addition of hydrochloric acid, to reduce the pH. Incubation of these supernatants, for example at 37° C. overnight, allows for acid-catalyzed lactonization, resulting in improved titers of 3-HBL. FIG. 12 depicts the 3-hydroxyalkanoic acid pathway scheme for DHBA and 3-HBL production, highlighting the branch point at DHBA-CoA. The observation that in the absence of tesB, more 3-HBL is produced while little DHBA is made, suggests that DHBA-CoA can self-lactonize into 3-HBL in vivo.

In some embodiments, acid post-treatment of culture supernatants increases 3-HBL titer by greater than 10%. In other embodiments, acid post-treatment of culture supernatants increases 3-HBL titer by greater than 100%. For example, 3-HBL titers can be increased by approximately 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250% or more than 250% including any intermediate values. In some embodiments, acid post-treatment of culture supernatants leads to a reduction in titer of DHBA of greater than 10%. For example, titer of DHBA can be reduced by approximately 10%, 20%, 30%, 40%, 50%, 60%, 70%, 80%, 85%, 90%, 95% or more than 95% including any intermediate values.

The liquid cultures used to grow cells associated with the invention can be housed in any of the culture vessels known and used in the art. In some embodiments large scale production in an aerated reaction vessel such as a stirred tank reactor can be used to produce large quantities of DHBA and/or 3-HBL.

Aspects of the invention include strategies to optimize production of DHBA and/or 3-HBL from a cell. Optimized production of DHBA and/or 3-HBL refers to producing a higher amount of a DHBA and/or 3-HBL following pursuit of an optimization strategy than would be achieved in the absence of such a strategy. One strategy for optimization is to increase expression levels of one or more genes associated with the invention through selection of appropriate promoters and ribosome binding sites. In some embodiments this may include the selection of high-copy number plasmids, or low or medium-copy number plasmids. In some embodiments the plasmid is a medium-copy number plasmid such as pETDuet. The step of transcription termination can also be targeted for regulation of gene expression, through the introduction or elimination of structures such as stem-loops.

In some embodiments it may be advantageous to use a cell that has been optimized for production of DHBA and/or 3-HBL. In some embodiments, screening for mutations that lead to enhanced production of DHBA and/or 3-HBL may be conducted through a random mutagenesis screen, or through screening of known mutations. In some embodiments shot-gun cloning of genomic fragments could be used to identify genomic regions that lead to an increase in production of DHBA and/or 3-HBL, through screening cells or organisms that have these fragments for increased production of DHBA and/or 3-HBL. In some cases one or more mutations may be combined in the same cell or organism.

Figure 10:
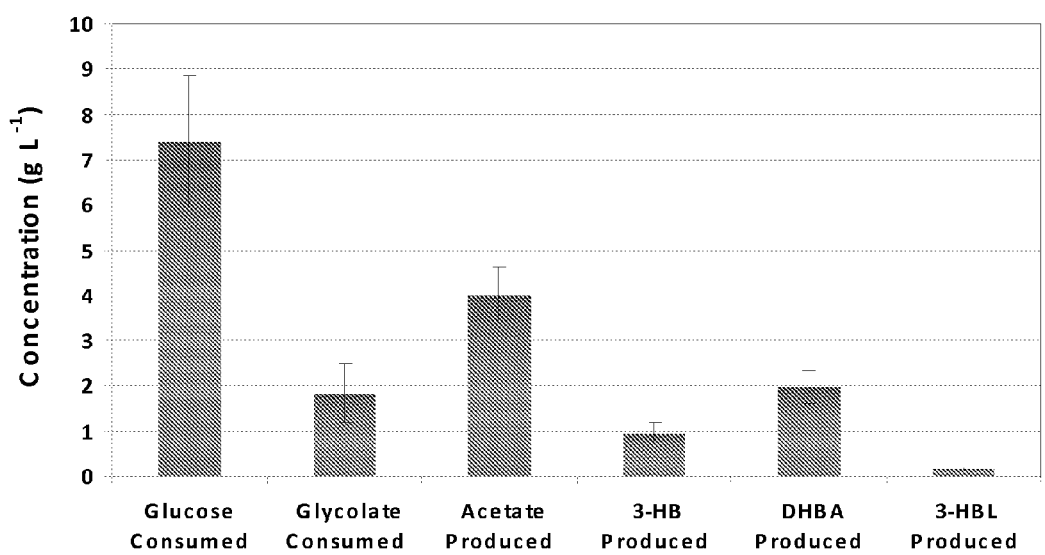
FIG. 10 depicts the production profile of the 3-hydroxyalkanoic acid pathway in recombinant *E. coli* MG1655(DE3) expressing bktB, phaB, pct, and tesB after 96 hours. The average levels of glucose and glycolate consumed, along with the average levels of acetate, 3HB, DHBA, and 3-HBL produced are shown for 11 independent cultures, with the error bars representing the standard deviation.

Optimization of production of DHBA and/or 3-HBL can involve optimizing selection of bacterial strains for expression of recombinant pathways described herein. In some embodiments, use of a bacterial strain that is close to wild-type, meaning a strain that has not been substantially genetically modified, may lead to increased titers of DHBA and/or 3-HBL. For example, in some embodiments, use of a bacterial strain which expresses recA and/or endA genes, such as E. coli strain MG1655(DE3) leads to increased titers of DHBA and/or 3-HBL (FIG. 10). As demonstrated in the Examples section, in some embodiments, use of E. coli MG1655(DE3) can lead to titers of 1.99±0.36 g $L^{-1}$ and 0.16±0.04 g $L^{-1}$ of DHBA and 3-HBL respectively, representing an approximate 3-fold increase in DHBA production relative to MG1655(DE3) recA$^-$ endA$^-$. In certain embodiments, titers of approximately 3.20 g $L^{-1}$ DHBA and approximately 0.23 g $L^{-1}$ 3-HBL can be produced using E. coli MG1655(DE3). Following acid-catalyzed lactonization, the titer of DHBA can be reduced to approximately 0.42 g $L^{-1}$ and the titer of 3-HBL can be increased to approximately 2.17 g $L^{-1}$.

Stereochemistry of molecules produced through the recombinant pathways described herein can be controlled by the choice of 3-hydroxybutyryl-CoA reductase. In certain embodiments, the use of PhaB results in (R)-3-hydroxyacids while the use of Hbd results in the (S) stereoisomer. In some embodiments, (S)-DHBA and/or (S)-3-HBL are produced, while in other embodiments, (R)-DHBA and/or (R)-3-HBL are produced. Methods and compositions described herein can also be applied to screen for an enzyme with similarity to hbd, with similar stereochemical preference but with an increased substrate range for the production of (R)-DHBA and (R)-3-HBL.

Optimization of protein expression may also require in some embodiments that a gene encoding an enzyme be modified before being introduced into a cell such as through codon optimization for expression in a bacterial cell. Codon usages for a variety of organisms can be accessed in the Codon Usage Database (kazusa.or.jp/codon/).

In some embodiments protein engineering can be used to optimize expression or activity of one or more enzymes associated with the invention. In certain embodiments a protein engineering approach could include determining the 3D structure of an enzyme or constructing a 3D homology model for the enzyme based on the structure of a related protein. Based on 3D models, mutations in an enzyme can be constructed and incorporated into a cell or organism, which could then be screened for an increased production of DHBA and/or 3-HBL. In some embodiments production of DHBA and/or 3-HBL in a cell could be increased through manipulation of enzymes that act in the same pathway as the enzymes associated with the invention. For example in some embodiments it may be advantageous to increase expression of an enzyme or other factor that acts upstream of a target enzyme such as an enzyme associated with the invention. This could be achieved by over-expressing the upstream factor using any standard method.

Methods and compositions described herein for the production of 3-hydroxyacids such as 3-HBL and DHBA from sugars and sugar-derived substrates have widespread applications. For example, 3-HBL is used in the pharmaceutical industry as a building block for cholesterol-reducing statins such as CRESTOR® and LIPITOR®, antibiotics such as ZYBOX®, the anti-hyperlipidemic medication EZETIIVI-IBE® (Lee et al., 2008; Lee and Park, 2009), HIV inhibitors (Kim et al., 1995) and the nutritional supplement carnitine (Wang and Hollingsworth, 1999b).

EXAMPLES

Example 1

Production of Hydroxyacids in E. coli

Herein, the 3HB pathway was used to produce complex 3-hydroxyacids—specifically 3HV, DHBA and 3-HBL. Also, the lactonization of DHBA to 3-HBL was investigated in detail. These products were made by supplying the non-natural substrates propionate (for 3HV production) or glycolate (for DHBA and 3-HBL production) to the 3HB pathway. These non-natural substrates were thiolated by propionyl-CoA transferase (pct) to form CoA thioesters capable of condensing with acetyl-CoA to eventually form the novel hydroxyacid products. For 3HV production, titers of 537 mg $L^{-1}$ of (R)-3HB and 522 mg $L^{-1}$ of (S)-3HV were achieved. For DHBA production, 3.2 g $L^{-1}$ of DHBA along with 230 mg $L^{-1}$ of 3-HBL were produced. The DHBA/3-HBL product profile can be shifted towards 3-HBL in one of two ways—by either removing the tesB gene and allowing for the auto-lactonization of DHBA-CoA or by treating DHBA-rich culture supernatants with acid to chemically lactonize the DHBA into 3-HBL. Removing the tesB gene resulted in an average improvement in 3-HBL production of 52%. The latter method of chemically lactonizing the culture supernatant with acid yielded 420 mg $L^{-1}$ of DHBA and 2.17 g $L^{-1}$ of 3-HBL, a 9-fold improvement in 3-HBL titer.

Hydroxyacids are versatile, chiral compounds that contain both a carboxyl and a hydroxyl moiety, readily allowing for their modification into several useful derivatives (Lee et al., 2002; Chen and Wu, 2005) and making them suitable for applications in the synthesis of antibiotics (Chiba and Nakai, 1985), β- and γ-aminoacids and peptides (Park, et al. 2001; Seebach et al., 2001), and as chiral synthetic building blocks (Lee et al., 2002). Direct biological production of hydroxyacid monomers has been successfully demonstrated for 3HB, and titers of 3 g $L^{-1}$ and 12 g $L^{-1}$ on the shake flask and fed-batch scales have been reported (Gao et al., 2002). In these reports, 3HB is made from acetyl-CoA through the use of acetyl-CoA acetyltransferase (phbA), 3-hydroxybutyryl-CoA dehydrogenase (phbB), phosphotransbutyrylase (ptb), and butyrate kinase (buk) (Liu and Steinbüchel, 2000a; Liu and Steinbüchel, 2000b; Gao et al., 2002). The last two of these enzymes were chosen to remove the CoA moiety from 3-hydroxybutyryl-CoA to yield free 3HB and were taken from *Clostridium acetobutylicum*, where they participate in the production of butyrate from butyryl-CoA (Liu and Steinbüchel, 2000b). Recently, thioesterase II (tesB) from *Escherichia coli* K12 (Naggert et al., 1991) was successfully employed to directly hydrolyze the acyl-thioester of 3HB-CoA (Liu et al., 2007; Tseng et al., 2009).

The success of direct production of 3HB from the condensation of two acetyl-CoA moieties opens up the possibility of producing more structurally diverse hydroxyacids through generalizing this pathway to the condensation of an acyl-CoA molecule with acetyl-CoA (FIG. 1). In the generalized 3HB pathway, referred to as the 3-hydroxyalkanoic acid pathway, one of the three acetoacetyl-CoA thiolases (thil, bktB, or phaA) was employed to perform the condensation reaction to yield a 3-ketoacyl-CoA intermediate, which was subsequently reduced by either phaB or hbd to yield a 3-hydroxyacyl-CoA compound. Finally, tesB was used to hydrolyze the CoA moiety from the 3-hydroxyacyl-CoA, liberating the free 3-hydroxyacid. These steps are the same as those described herein for 3HB biosynthesis. One additional complication in the 3-hydroxyalkanoic acid pathway is that unlike acetyl-CoA, short chain acyl-CoA compounds that would be candidate substrates for this pathway are not readily available metabolites in *E. coli*. To circumvent this, propionyl-CoA transferase (pct), a broad substrate-specificity enzyme from *Megasphaera elsdenii* (Schweiger and Buckel, 1984; Taguchi et al., 2008) that exchanges CoA moieties between short-chain organic acids, was employed. In the 3-hydroxyalkanoic acid pathway, pct was used to transfer CoA from acetyl-CoA to an acid supplied to the cell (such as propionate), forming the acyl-CoA required by the pathway. Table 1 summarizes the characteristics and sources for each enzyme employed in the 3-hydroxyalkanoic acid pathway shown in FIG. 1.

TABLE 1

General characteristics and sources of enzymes used in the 3-hydroxyalkanoic acid pathway shown in FIG. 1.

| Enzyme | Organism of Origin | Properties | Reference |
| --- | --- | --- | --- |
| atoB | *P. putida* KT2440 | Acetyltransferase, native to *P. putida* | Li, 1989 |
| bktB | *R. eutropha* H16 | Acetyltransferase, broad substrate range (C4-C6) | Slater et al. 1998 |
| hbd | *C. acetobutylicum* 824 | Dehydrogenase, forms S stereoisomer product | Boynton et al. 1996 |
| pct | *M. elsdenii* | CoA-transferase, wide substrate range ($C_2$-$C_4$) | Schweiger and Buckel, 1984 |
| phaA | *R. eutropha* H16 | Acetyltransferase, high activity and somewhat wide substrate range | Schubert et al. 1988 |
| phaB | *R. eutropha* H16 | Dehydrogenase, forms R stereoisomer product | Schubert et al. 1988 |
| S1 | *C. magnoliae* (Yeast) | Dehydrogenase, forms R stereoisomer product, strongly prefers electronegative group attached to the 4-position. | Yasohara, 2000 |

TABLE 1-continued

General characteristics and sources of enzymes used in the 3-hydroxyalkanoic acid pathway shown in FIG. 1.

| Enzyme | Organism of Origin | Properties | Reference |
| --- | --- | --- | --- |
| tesB | *E. coli* K12 | Thioesterase, Very broad substrate range (C4-C16) | Huisman et al. 1991 |
| thil | *C. acetobutylicum* 824 | Acetyltransferase, high activity | Stim-Herndon et al. 1995 |

Table 2 (from Schweiger and Buckel, 1984) summarizes specific and relative activities for inhibition of the CoA-transferase by carboxylic acid.

TABLE 2

| Group Carboxylic acid added | Specific Activity (units/mg) | Relative activity (%) |
| --- | --- | --- |
| None | 34.1 | 100 |
| (R)-Lactate | 9.1 | 27 |
| (S)-Lactate | 15.8 | 46 |
| Acrylate | 12.7 | 37 |
| Propionate | 6.8 | 20 |
| Butyrate | 9.6 | 28 |
| Fumarate | 32.8 | 96 |
| Succinate | 29.6 | 87 |
| (R)-2-Hydroxyglutarate | 29.6 | 87 |
| (E)-Glutaconate | 32.1 | 94 |

A goal of the work described herein was to use the 3-hydroxyalkanoic acid pathway to synthesize 3-hydroxybutyrolactone (3-HBL) and/or its hydrolyzed form 3,4-dihydroxybutyric acid (DHBA) from sugars and sugar-derived substrates. 3-HBL is widely used in the pharmaceutical industry as a building block for the class of cholesterol-reducing drugs called statins such as CRESTOR® and LIPITOR® as well as the antibiotic ZYBOX® the anti-hyperlipidemic medication EZETIMIBE® (Lee et al., 2008; Lee and Park, 2009). Other pharmaceuticals derived from 3-HBL include HIV inhibitors (Kim et al., 1995) and the nutritional supplement carnitine (Wang and Hollingsworth, 1999b). 3-HBL has been listed as one of the top ten value-added chemicals by the U.S. Department of Energy (Werpy and Peterson, 2004). 3-HBL can readily be transformed into a variety of three-carbon building blocks (Wang and Hollingsworth, 1999a). Herein, the production of 3-hydroxyvalerate (3HV) from glucose and propionate was first examined to test the ability of the hydroxyalkanoic acid pathway to uptake free acids and convert them to CoA thioesters. Next, DHBA and 3-HBL biosynthesis from glucose and glycolate was investigated and factors controlling the titers of and ratio between these two products were examined.

Results

Production of 3HV from Glucose and Propionate

Figure 3:
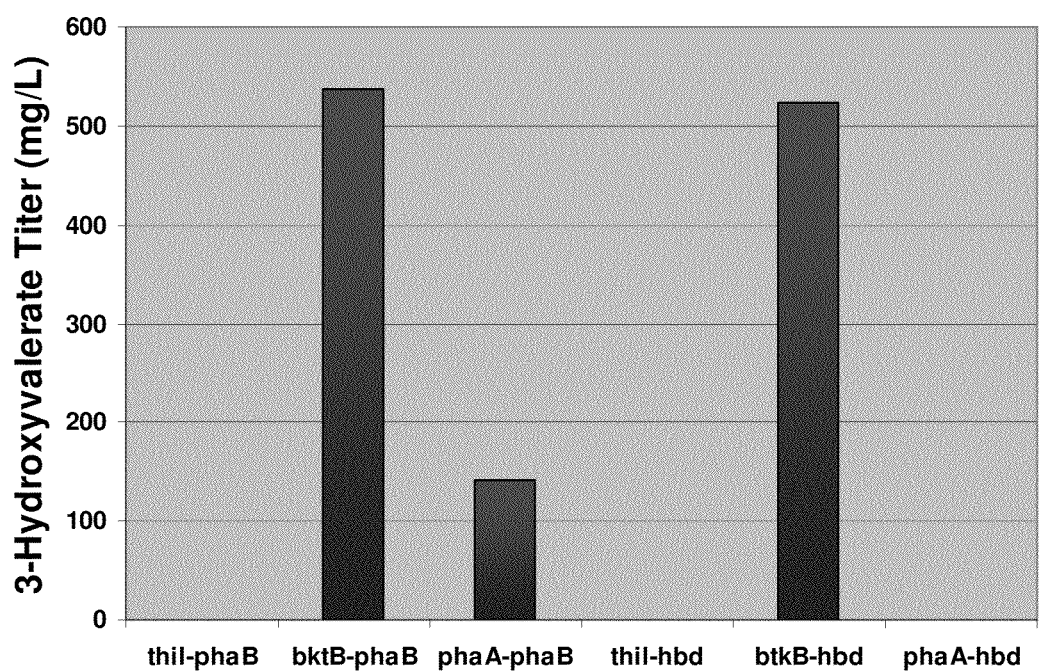
FIG. 3 is a graph depicting production of 3HV by recombinant *E. coli* expressing tesB, pct, one of three acetoacetyl-CoA thiolases (thil, bktB, or phaA), and one of two 3-hydroxybutyryl-CoA reductases (phaB or hbd).

The 3-hydroxyalkanoic acid pathway was first tested using propionate as a substrate. Neutralized propionate was supplied along with glucose to recombinant *E. coli* cells expressing one of three acetoacetyl-CoA thiolases (thil, bktB, or phaA), one of two 3-hydroxybutyryl-CoA reductases (phaB or hbd), tesB, and pct. These cultures were incubated for 48 hours at 30° C., and the resulting 3HV titers were measured by HPLC (FIG. 3). 3HV was detected in cultures expressing bktB-phaB (537 mg $L^{-1}$), phaA-phaB (142 mg $L^{-1}$), and bktB-hbd (522 mg $L^{-1}$). No 3HV was detected in the other three gene combinations. The result that pathways with bktB yield the highest 3HV titer is consistent with reports that BktB has high activity towards the condensation of a $C_3$ substrate with a $C_2$ to form a $C_5$ product (Slater et al., 1998). The choice of reductase in the 3-hydroxyalkanoic acid pathway did not significantly influence 3HV production, except in the case of phaA, where 3HV was only detected in the phaA-phaB gene combination.

Chiral Analysis of Microbially-Produced 3HV

Recombinant *E. coli* expressing the 3-hydroxyalkanoic acid pathway expressing bktB and either phaB or hbd as the 3-hydroxybutyryl-CoA reducase was grown at 30° C. in 50 mL LB supplemented with 20 g $L^{-1}$ glucose and 20 mM propionate for 48 hours. The stereochemistry of the resulting 3HV in the media from these cultures was determined by methyl esterification of the 3HV present followed by chiral HPLC analysis as described in the Materials and Methods section. These spectra were compared to a racemic 3HV standard. The results confirm that 3-hydroxyalkanoic acid pathways expressing phaB make a different stereoisomer of 3HV than pathways employing hbd (FIG. 4). The lack of an enantiopure 3HV standard prevents the assignment of absolute stereochemistry (e.g. R or S) to each sample, though it is clear that the phaB and hbd cultures produce different stereoisomers. However, based on previous reports regarding the product stereochemistry of phaB and hbd (Lee et al., 2008; Liu et al., 2007) and the observation that (R)-3HB has a faster retention time relative to (S)-3HB, it is highly likely that here the phaB pathway sample is making (R)-3HV while the hbd pathway sample produces (S)-3HV.

Production of DHBA and 3-HBL from Glucose and Glycolate

Figure 5:
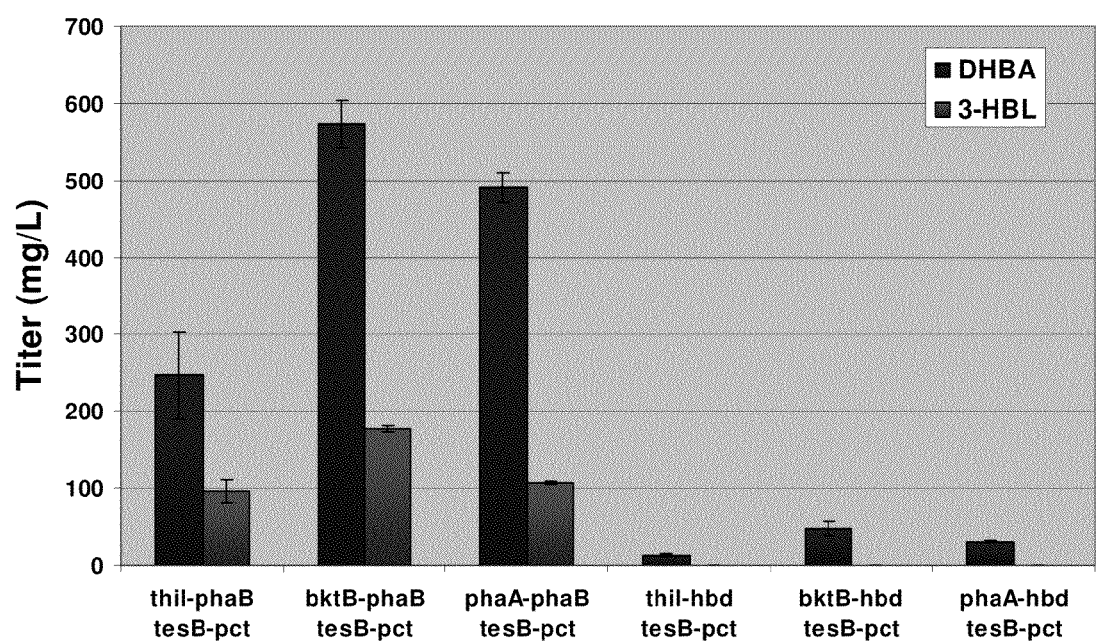
FIG. 5 depicts production of DHBA (left bars) and 3-HBL (right bars) by recombinant MG1655(DE3) endA⁻ recA⁻ *E. coli* expressing different 3-hydroxyalkanoic acid pathway genes. The specific genes used in each pathway are shown on the x-axis.
Figure 6:
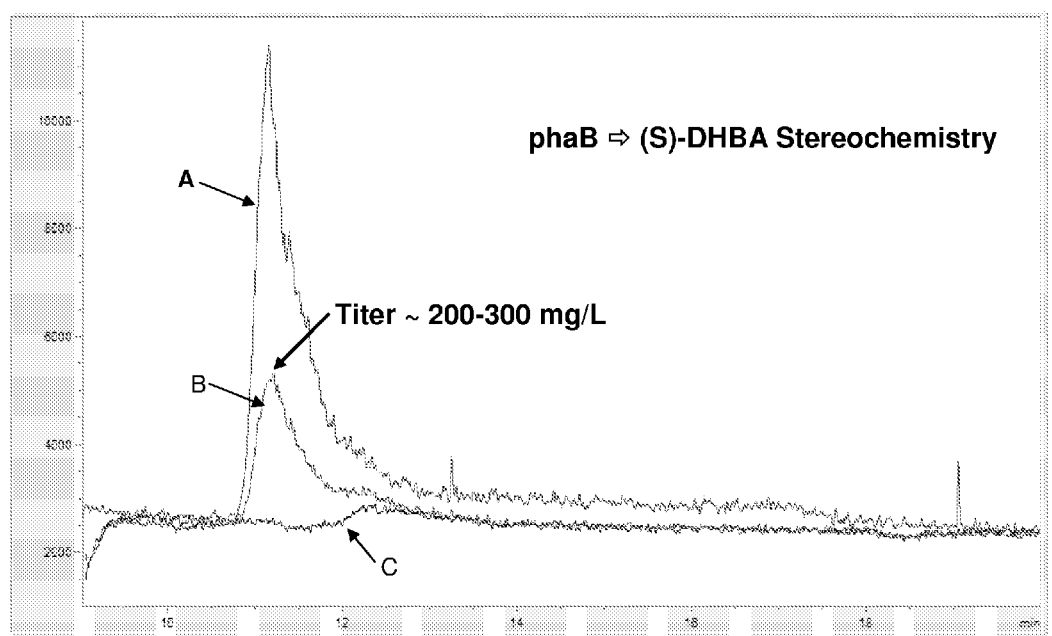
FIG. 6 is a graph indicating Liquid Chromatography—Mass Spectroscopy (LC/MS) spectra confirming production of DHBA produced by recombinant *E. coli*. Line "A" represents a DHBA standard, while line "B" is DHBA produced by recombinant *E. coli* expressing phaA, phaB, pct, and tesB. Line "C" is a negative control. The MS signal is an ion trace at m/z=138, which represents the ammonium adduct of protonated DHBA.
Figure 7:
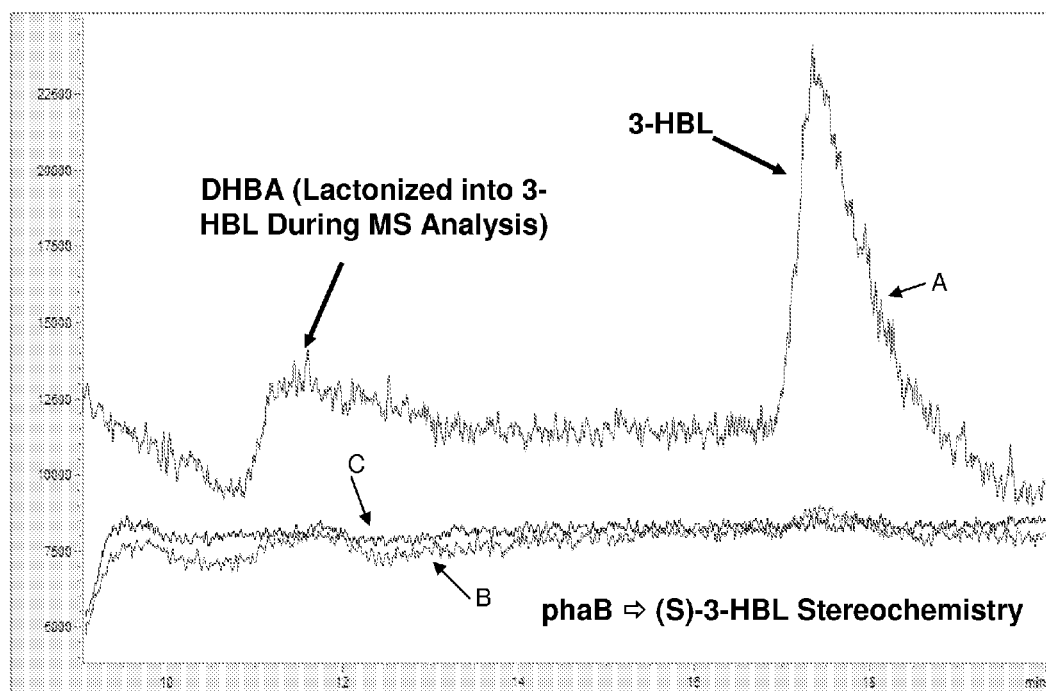
FIG. 7 is a graph indicating Liquid Chromatography—Mass Spectroscopy (LC/MS) spectra confirming production of 3-HBL produced by recombinant *E. coli*. Line "A" represents a 3-HBL+DHBA standard, while line "B" is 3-HBL produced by recombinant *E. coli* expressing phaA, phaB, pct, and tesB culture in the presence of glycolate and glucose. Line "C" is a negative control. The MS signal is an ion trace at m/z=120.

For the production of DHBA and 3-HBL, neutralized glycolate was supplied along with glucose to recombinant *E. coli* MG1655(DE3) recA⁻ endA⁻ cells expressing one of three acetoacetyl-CoA thiolases (thiI, bktB, or phaA), one of two 3-hydroxybutyryl-CoA reductases (phaB or hbd), tesB, and pct. These cultures were incubated for 96 hours at 30° C., and the resulting DHBA and 3HBL titers were measured by HPLC (FIG. 5). The identity of DHBA was confirmed through LC/MS analysis (FIG. 5). DHBA was detected in all 3-hydroxyalkanoic acid pathway gene combinations, however 3-HBL was only detected in pathways expressing phaB. The bktB-phaB combination yielded the highest DHBA and 3-HBL titers of 573±30 mg $L^{-1}$ and 178±4 mg $L^{-1}$ respectively. The phaA-phaB combination performed almost as well, yielding DHBA and 3-HBL titers of 492±19 mg $L^{-1}$ and 107±3 mg $L^{-1}$ respectively. The thiI-phaB combination was less efficient than the other phaB combinations, yielding only 247±57 mg $L^{-1}$ of DHBA and 96±14 mg $L^{-1}$ of 3-HBL. Pathway combinations using hbd made only DHBA, and the maximum DHBA titer of 47±10 mg $L^{-1}$ was from bktB-hbd.

Effect of tesB Expression on DHBA and 3-HBL Production

Figure 8:
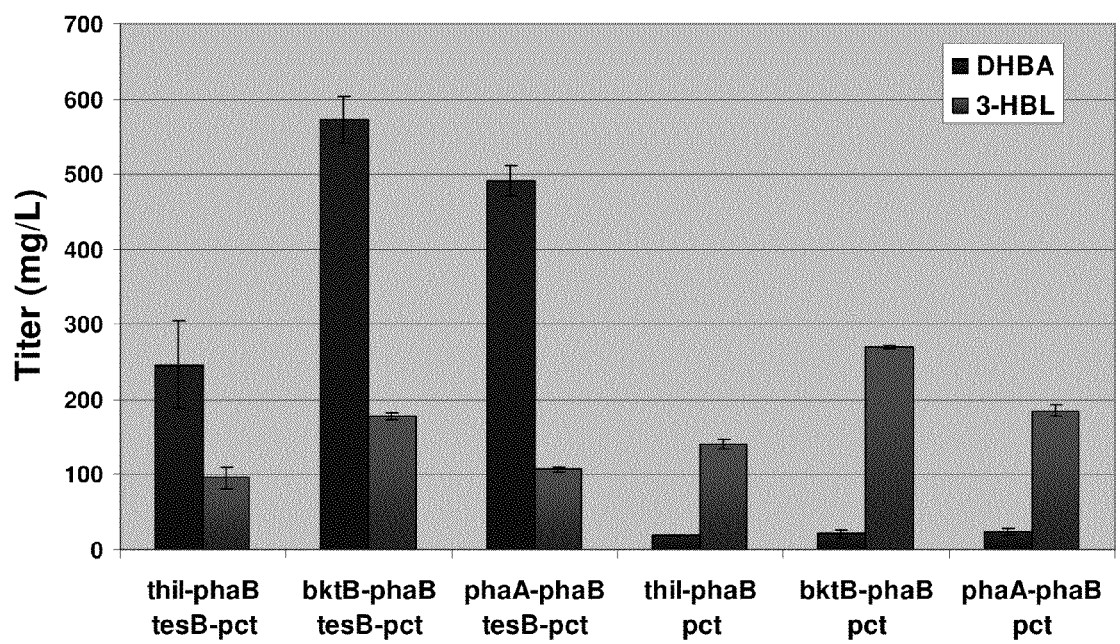
FIG. 8 depicts production of DHBA (left bars) and 3-HBL (right bars) by recombinant *E. coli* MG1655(DE3) endA⁻ recA⁻ expressing different 3-hydroxyalkanoic acid pathway genes in the presence or absence of tesB. The specific genes used in each pathway are shown on the x-axis.

The production of DHBA and 3-HBL was tested with and without tesB in 3-hydroxyalkanoic acid pathways co-expressing phaB, one of three acetoacetyl-CoA thiolases (thiI, bktB, or phaA), and pct. This experiment was conducted similar to the one above, but with the goal of understanding how 3-HBL was being produced by the 3-hydroxyalkanoic acid pathway. The resulting DHBA and 3-HBL titers are shown in FIG. 8. As is seen in this figure, pathways lacking tesB produced on average 57% more 3-HBL, but 95% less DHBA. The bktB-phaB-pct combination yielded the highest 3-HBL titer of 270±3 mg $L^{-1}$. The performance of pathways with different acetoacetyl-CoA thiolases followed that of FIG. 5, with bktB reaching the highest product titers and thiI having the lowest titers.

Effect of Acidic Post-Treatment on DHBA and 3-HBL Titers

Figure 9:
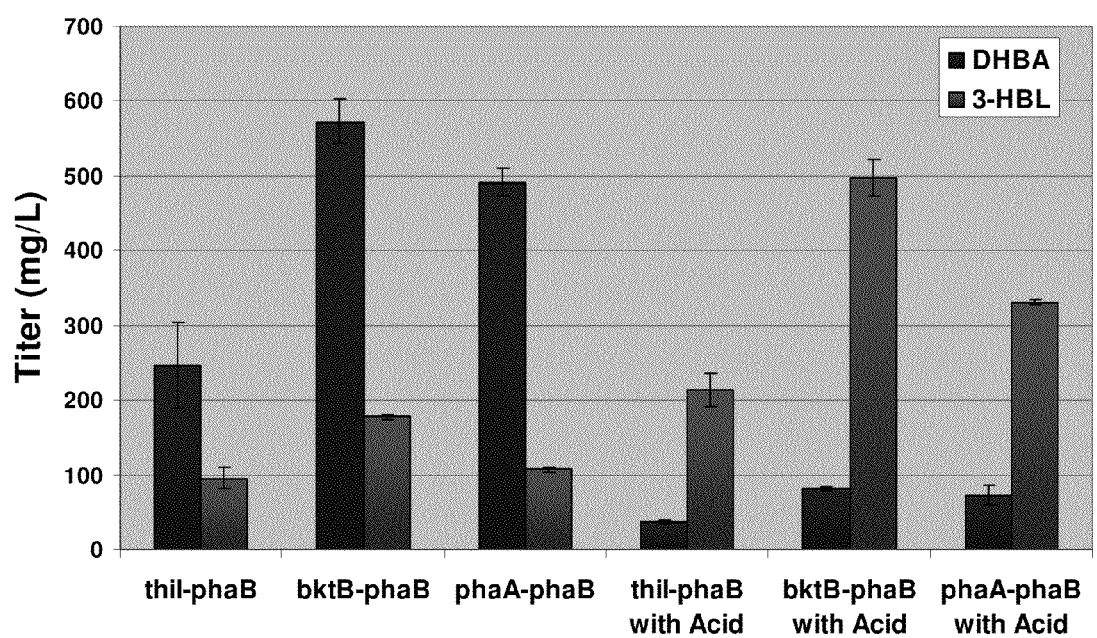
FIG. 9 depicts production of DHBA (left bars) and 3-HBL (right bars) by recombinant *E. coli* MG1655(DE3) endA⁻ recA⁻ expressing different 3-hydroxyalkanoic acid pathway genes along with tesB and pct. The right three samples represent product titers that result when the left three samples are treated with acid. The specific acetoacetyl-CoA thiolase and 3-hydroxybutyryl-CoA reductase used in each pathway are shown on the x-axis.

In organic chemistry, it is well documented that lactonization is acid-catalyzed (Carey, 2000). Since the phaB cultures shown in FIG. 5 produced much DHBA but relatively little 3-HBL, the 96-hour supernatants from these cultures were acidified with 50 mM of hydrochloric acid, reducing the pH below 1.0. These culture supernatants were then incubated at 37° C. overnight to allow for acid-catalyzed lactonization to occur. After this overnight incubation, these samples were subjected to HPLC analysis, and the resulting DHBA and 3-HBL titers are shown in FIG. 9. The acid post-treatment of the culture supernatants improved 3-HBL titers by 171% on average, and the highest 3-HBL titer obtained was 497±25 mg $L^{-1}$ for the bktB-phaB pathway combination. DHBA titers dropped by 85% on average during the process due to the lactonization of DHBA to 3-HBL. Approximately 80-85 mol % of the DHBA was converted to 3-HBL, with the remaining 15-20 mol % being lost presumably to DHBA multimerization.

Strain Effects on DHBA and 3-HBL Production

Figure 11:
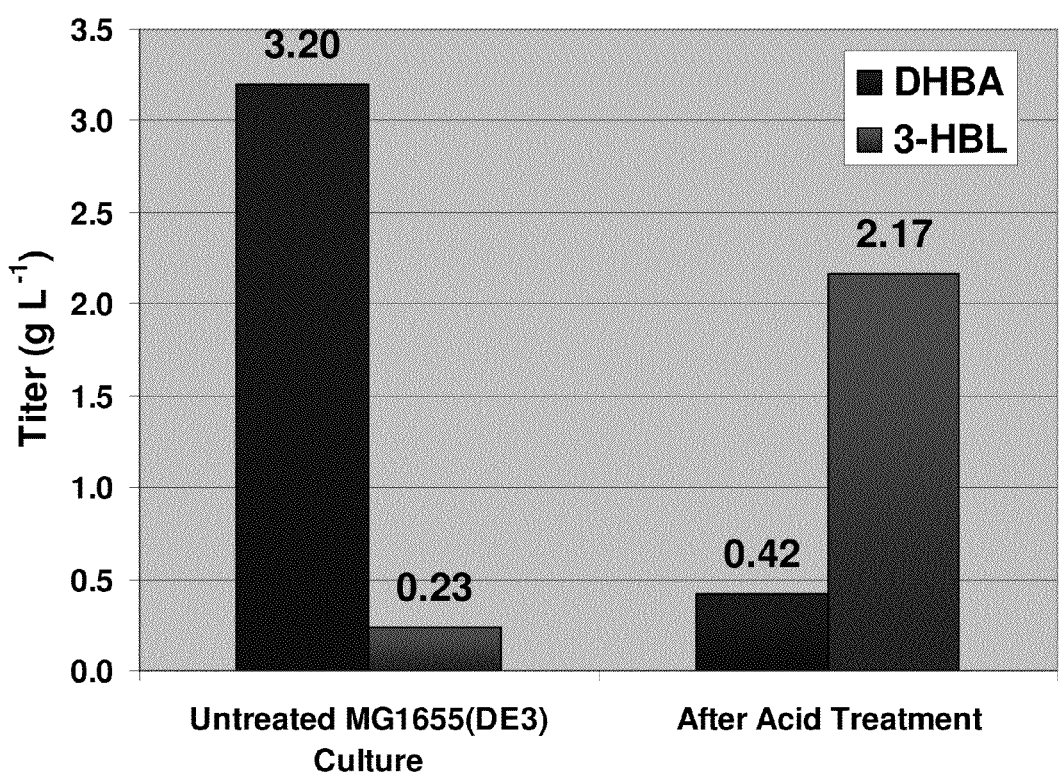
FIG. 11 depicts production of DHBA (left bars) and 3-HBL (right bars) in the highest-producing culture of recombinant *E. coli* MG1655(DE3) expressing bktB, phaB, pct, and tesB after 96 hours. This culture was subjected to an overnight acid treatment to catalyze lactonization, and the resulting DHBA and 3-HBL levels are shown on the right side of this figure.

The 3-hydroxyalkanoic acid pathway was further tested in *E. coli* MG1655(DE3) with intact recA and endA genes to see if the titers of DHBA and 3-HBL could be further improved in a more wild-type *E. coli* strain. The results of this experiment are shown in FIGS. 10 and 11. In FIG. 10, the total consumption of glucose and glycolate and the production of acetate, 3HB, DHBA, and 3-HBL for 11 independent cultures is shown. The relatively large sample size helps to counteract the natural variability in gene expression that occurs in recA strains. In this experiment, 1.99±0.36 g $L^{-1}$ of DHBA was produced along with 0.16±0.04 g $L^{-1}$ of 3-HBL. This represents more than a 3-fold improvement in DHBA production over MG1655(DE3) recA⁻ endA⁻ (FIG. 5). The highest DHBA producing culture made 3.20 g $L^{-1}$ of DHBA and 0.23 g $L^{-1}$ of 3-HBL (FIG. 11). This culture was subjected to overnight acid-catalyzed lactonization, resulting in 2.17 g $L^{-1}$ of 3-HBL with 0.42 g $L^{-1}$ of DHBA. Without wishing to be bound by any theory, the reason why MG1655(DE3) is a superior DHBA producer to MG1655(DE3) recA⁻ endA⁻ may be because the increased genetic engineering that the latter strain has been subjected to has negatively impacted its growth and metabolism.

Discussion

Controlling Product Profiles Through Selection of Pathway Enzymes

The 3-hydroxyalkanoic acid pathway has the advantage that it and its constituent enzymes are flexible with respect to their substrates—the pathway is highly versitile. In particular, TesB, PhaB, BktB, and Pct are all known to work with at least three different substrates (Huisman et al., 1991; Schubert et al., 1988; Slater et al., 1998; Schweiger and Buckel, 1984). Substrate flexibility was critical in realizing the production of 3HV, DHBA, and 3-HBL from this pathway. Experimentally, the combination of the four most flexible proteins (TesB, PhaB, BktB, and Pct) was found to yield the highest titers of novel 3-hydroxyalkanoic acid pathway products (FIGS. 4, 5, 8 and 9).

Furthermore, the products obtained through the 3-hydroxyalkanoic acid pathway can be precisely controlled through the substrates and genes supplied to the pathway. For instance, 3HV is only produced in the presence of propionate, while DHBA and 3-HBL are only made when glycolate is added. The pathway can also be modulated to produce more DHBA or 3-HBL through the presence or absence of the thioesterase TesB. With recombinant TesB, significantly more DHBA was made (573 mg $L^{-1}$ for the bktB-phaB pathway combination) than 3-HBL (178 mg $L^{-1}$). Without TesB, more 3-HBL was made (270 mg $L^{-1}$ for bktB-phaB) than DHBA (21 mg $L^{-1}$). The small amount of DHBA formed in the absence of recombinant tesB may be due to the expression of genomic tesB, as this gene is native to *E. coli* (Huisman et al., 1991). Nonetheless, this result suggests that without a thioesterase to hydrolyze the CoA thioester of DHBA (DHBA-CoA), DHBA-CoA can self-lactonize into 3-HBL in vivo (FIG. 12). While it is not known whether there is an enzyme in *E. coli* that catalyzes this reaction or whether this reaction occurs spontaneously in vivo, it is clear that 3-HBL is produced from glucose and glycolate and that tesB plays an important role in determining the fate of the DHBA-CoA intermediate (FIG. 8).

Figure 13:
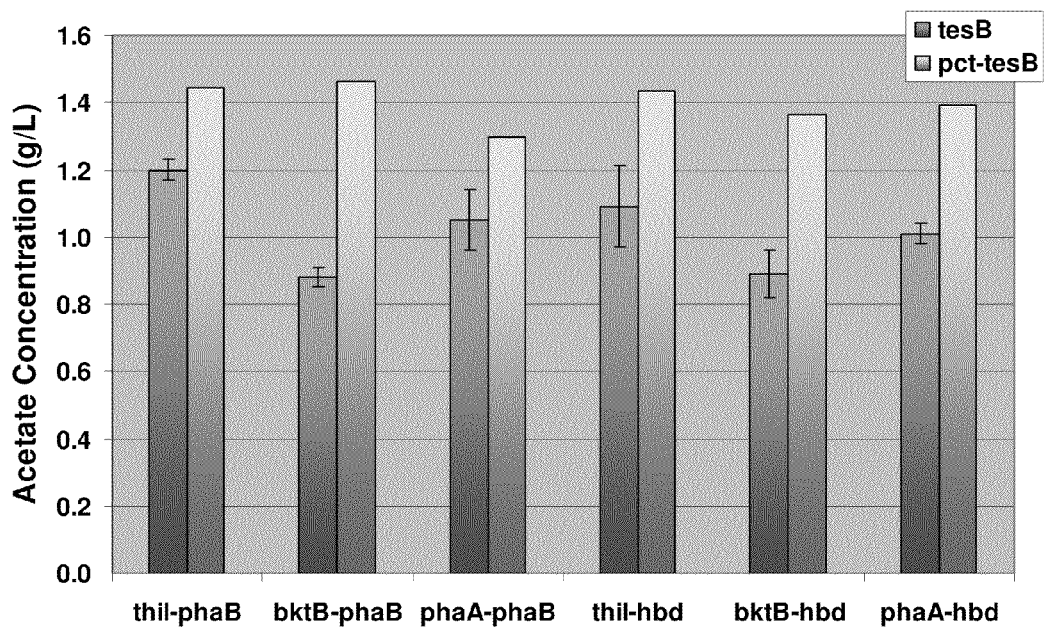
FIG. 13 depicts acetate production after 48 hours from the 3-hydroxyalkanoic acid pathway in *E. coli* MG1655(DE3) recA⁻ endA⁻ with (right bars, pct-tesB) and without pct (left bars, tesB). Experiments without the pct were performed in triplicate, while those with pct represent single trials.

In all of the 3HV, DHBA, and 3-HBL production experiments done in MG1655(DE3) recA$^-$ endA$^-$, very little 3HB (<100 mg L$^{-1}$) was detected. Even in MG1655(DE3), there was twice as much DHBA produced relative to 3HB (FIG. 11), even though 3HB is the natural product for the enzymes employed in the 3-hydroxyalkanoic acid pathway. 3HB is made from the condensation of two acetyl-CoA moieties and should theoretically be a major side product in the production of the other 3-hydroxyacids in this work since 3HB is the natural product of the action of acetoacetyl-CoA thiolases with 3-hydroxybutyryl-CoA reductases and 3HB has been produced at 2-3 g L$^{-1}$ with these enzymes (Tseng et al., 2009). The only difference between the 3HB and 3-hydroxyalkanoic acid pathways is the presence of pct in the latter pathway. Pct is a CoA-transferase that exchanges CoA moieties between short-chain organic acids, including acetate and acetyl-CoA (Schweiger and Buckel, 1984). That very little 3HB is made in the presence of recombinant pct suggests that the Pct protein may be removing CoA from acetyl-CoA in the cell and transferring it onto other acids, including propionate for 3HV production and glycolate for DHBA and 3-HBL production. This CoA transfer could significantly reduce intracellular acetyl-CoA concentrations, making the second-order condensation of two acetyl-CoA molecules much less likely than the condensation of acetyl-CoA with another acyl-CoA (a first-order reaction with respect to acetyl-CoA). A byproduct of removing CoA from acetyl-CoA would be increased acetate production, and this effect was confirmed by HPLC in comparing the 3-hydroxyalkanoic acid pathway with and without pct (FIG. 13). The significant increase in acetate production corroborates the hypothesis that Pct is harvesting CoA from acetyl-CoA for use in thiolating other short-chain acids within the cell. This action likely reduces acetyl-CoA levels to the point that 3HB biosynthesis is significantly inhibited.

Controlling Stereochemistry via Choice of 3-Hydroxybutyryl-CoA Reductase

The 3-hydroxyalkanoic acid pathway's flexibility also extends to the stereochemistry of its final product—by using phaB or hbd as the 3-hydroxybutyryl-CoA reductase in the pathway, different stereochemical outcomes can be realized. It is well documented in the literature that PhaB results in (R)-3-hydroxyacids while Hbd results in the (S) stereoisomer (Lee et al., 2008; Liu et al., 2007). This phenomenon was experimentally verified both in pathways producing 3HB (Tseng et al., 2009) and 3HV (FIG. 4). The methyl esterification chiral analysis method used to analyze the stereochemistry of 3HB and 3HV does not work on DHBA because of its ability to lactonize and because of the inability of the 3-HBL lactone stereoisomers to resolve from one another during the analysis. However, based on the observation that PhaB and Hbd produce different and completely enantiopure 3HB and 3HV products, there is no reason to expect that they will not do the same for DHBA and 3-HBL. Interestingly, because DHBA has a hydroxyl group in the 8-position that changes the stereochemical priority of the different parts of the molecule about its stereocenter, the stereochemistry of DHBA formed by PhaB should be (S)-DHBA while that formed by Hbd should be (R)-DHBA. This assignment of stereochemistry is based on the absolute position of the γ-hydroxyl group in DHBA relative to the carboxylate group. Since PhaB is more efficient than Hbd at producing DHBA and 3-HBL in the 3-hydroxyalkanoic acid pathway (FIG. 5), the pathway is better suited for the production of (S)-DHBA and (S)-3-HBL than the (R) stereoisomers. Fortunately, the (S) stereoisomer is predominately used in the production of pharmaceuticals and high-value compounds (Lee and Park, 2009). The screening of hbd homologs could identify a 3-hydroxybutyryl-CoA reductase with identical stereochemical preference but with an increased substrate range for the production of (R)-DHBA and (R)-3-HBL.

Conclusions

In this work, 3HV (0.54 g L$^{-1}$), DHBA (3.2 g L$^{-1}$), and 3-HBL (2.2 g L$^{-1}$) were produced using the 3-hydroxyalkanoic acid pathway (FIG. 1) in *E. coli*. These compounds have applications ranging from chiral building blocks to polymeric materials to high-value pharmaceuticals. This work represents one of the first reports on 3HV biosynthesis in *E. coli*, and is the first report on the complete biological production of DHBA and 3-HBL from inexpensive sugar and sugar-derived substrates. Further screening of additional 3-hydroxyalkanoic acid pathway homologs should provide a rich resource of pathway combinations for the production of other high value 3-hydroxyacids such as 3-hydroxypropionate from formyl-CoA and acetyl-CoA. Molecular analogs of DHBA and 3-HBL could be made using the 3-hydroxyalkanoic acid pathway as well, such as 3,4-dihydroxyvalerate and 4-methyl-3-HBL from the condensation of lactyl-CoA and acetyl-CoA, potentially leading to new intermediates for more effective pharmaceuticals.

Product titers from the 3-hydroxyalkanoic acid pathway could be further enhanced by additional optimization of culture conditions and host strain. The screening of homologous pathway enzymes could improve titers in addition to broadening the substrate range of the pathway. One promising route for increasing productivity is to engineer *E. coli* to produce pathway substrates "in-house." For instance, glycolate could be made intracellularly from glyoxylate through the action of the ycdW glyoxylate reductase gene (Nunez et al., 2001). Intracellular production of pathway substrates would eliminate the need for substrate transport across the cellular envelope, accelerating production. Intracellular production of substrates would also allow the feeding of just glucose to *E. coli* for product formation, simplying the bioprocess while lowering material costs.

Materials and Methods

Strains and Chemicals

*E. coli* DH10B (Invitrogen, Carlsbad, Calif.) and Electro-Ten-Blue (Stratagene, La Jolla, Calif.) were used for transformation of cloning reactions and propagation of all plasmids. *E. coli* MG1655(DE3) was constructed from *E. coli* MG1655 using a XDE3 Lysogenization Kit (Novagen, Darmstadt, Germany). The recA and endA genes in *E. coli* MG1655(DE3) were then knocked out by the method of Datsenko and Wanner (2000), to yield *E. coli* MG1655(DE3) recA$^-$ endA$^-$ (Tseng et al., 2009). Both *E. coli* MG1655 (DE3) and *E. coli* MG1655(DE3) recA$^-$ endA$^-$ were used for the production of 3HV, DHBA, and 3-HBL. Luria-Bertani (LB) medium, D-glucose, propionic acid, and glycolic acid were purchased from BD Biosciences (Sparks, Md.), Mallinckrodt Chemicals (Phillipsburg, N.J.), Sigma-Aldrich (St. Louis, Mo.), and MP Biomedicals (Solon, Ohio), respectively. Unless otherwise noted, all chemicals were purchased at the highest grade available.

Plasmids and Primers

Genes derived from *C. acetobutylicum* ATCC 824 (thil and hbd), *R. eutropha* H16 (phaA, bktB, and phaB), *E. coli* K-12 (tesB), and *M. elsdenii* (pct) were obtained by polymerase chain reaction (PCR) using genomic DNA (gDNA) templates. All gDNAs were prepared using the Wizard Genomic DNA Purification Kit (Promega, Madison, Wis.). Custom oligonucleotides (primers) were purchased for all PCR amplifications (Sigma-Genosys, St. Louis, Mo.) and are shown in Table 3. In all cases, HotStar HiFidelity Polymerase (Qiagen, Valencia, Calif.) was used for DNA amplification. Restriction enzymes and T4 DNA ligase were purchased from New England Biolabs (Ipswich, Mass.). DNA digestions, ligations, and transformations were performed according to standard procedures (Sambrook and Russell, 2001).

Two co-replicable vectors, pETDuet-1 and pCDFDuet-1 (Novagen, Darmstadt, Germany), were used for construction of the 3-hydroxyalkanoic acid pathways. Both Duet vectors contain two multiple cloning sites (MCS), each of which is preceded by a T7lac promoter and a ribosome binding site (RBS), affording high-level expression of each individual gene. For cloning the pathway genes into these vectors, PCR products were made using 5' and 3' primers with desired restriction sites incorporated within them. These sites, used for cloning the genes, are underlined in Table 3. These PCR products were digested with restriction enzymes corresponding to the restriction site incorporated into them by their respective primers and ligated directly into similarly digested Duet vector. Ligation reactions using pETDuet-1 as the vector were transformed into DH10B *E. coli*, while ligations using pCDFDuet-1 were transformed into ElectroTen-Blue *E. coli*. One of three acetoacetyl-CoA thiolases (thil, bktB, and phaA) and one of two 3-hydroxybutyryl-CoA reductases (phaB and hbd) were cloned into pETDuet-1, resulting in six pETDuet-based plasmids. The pCDFDuet-based plasmids contained either pct and tesB or just pct alone. Once all plasmids were constructed, one pETDuet-based plasmid and one pCDFDuet-based plasmid were co-transformed into *E. coli* MG1655(DE3) recA⁻ endA⁻ or *E. coli* MG1655(DE3) to create a complete 3-hydroxyalkanoic acid pathway-expressing production strain.

TABLE 3

List of DNA oligonucleotide primers used in the cloning of genes for the 3-hydroxyalkanoic acid project. Restriction sites used for cloning are underlined. Primer names correspond to the name of the gene that the primer amplifies, whether the primer is the forward primer (FP) or reverse primer (RP) of that gene, and the restriction site incorporated into the primer sequence for cloning.

| Primer | Sequence 5'→3' | Source |
| --- | --- | --- |
| bktB-FP-NcoI | GACACCATGGGCATGACGCGTGAAGTGGTAG (SEQ ID NO: 10) | Sigma-Genosys |
| bktB-RP-EcoRI | GACAGAATTCTCAGATACGCTCGAAGATGG (SEQ ID NO: 11) | Sigma-Genosys |
| hbd-FP-NdeI | TATCCATATGAAAAAGGTATGTGTTATAGGTGC (SEQ ID NO: 12) | Sigma-Genosys |
| hbd-RP-XhoI | GACACTCGAGTTATTTTGAATAATCGTAGAAACCTTTTC (SEQ ID NO: 13) | Sigma-Genosys |
| phaA-FP-NcoI | GACACCATGGGCATGACTGACGTTGTCATCGTATC (SEQ ID NO: 1) | Sigma-Genosys |
| phaA-RP-EcoRI | GACAGAATTCTTATTTGCGCTCGACTGC (SEQ ID NO: 2) | Sigma-Genosys |
| phaB-FP-NdeI | GACACATATGACTCAGCGCATTGC (SEQ ID NO: 3) | Sigma-Genosys |
| phaB-RP-XhoI | GACACTCGAGTCAGCCCATGTGCAGG (SEQ ID NO: 4) | Sigma-Genosys |
| pct-FP-EcoRI | GACAGAATTCATGAGAAAAGTAGAAATCATTACAGCTG (SEQ ID NO: 7) | Sigma-Genosys |
| pct-RP-PstI | GACACTGCAGTTATTTTTTCAGTCCCATGGG (SEQ ID NO: 8) | Sigma-Genosys |
| tesB-FP-NdeI | GACACATATGAGTCAGGCGCTAAAAAAAT (SEQ ID NO: 5) | Sigma-Genosys |
| tesB-RP-XhoI | GACACTCGAGTTAATTGTGAATTACGCATCACC (SEQ ID NO: 6) | Sigma-Genosys |
| thil-FP-NcoI | GACACCATGGGCATGAGAGATGTAGTAATAGTAAGTGCTGTAAGA (SEQ ID NO: 14) | Sigma-Genosys |
| thil-RP-EcoRI | GACAGAATTCTATTTAGTCTCTTTCAACTACGAGAGC (SEQ ID NO: 15) | Sigma-Genosys |

Culturing Conditions

Recombinant *E. coli* harboring one of the acetoacetyl-CoA thiolases (thil, bktB, or phaA) and one of two 3-hydroxybutyryl-CoA reductases (phaB or hbd) on the pETDuet-1 vector and tesB and/or pct on the pCDFDuet-1 vector were cultured in 50 mL LB supplemented with 1% glucose in a 250 mL shake flask at 30° C. unless otherwise indicated in the text. Ampicillin (50 mg L$^{-1}$) and streptomycin (50 mg L$^{-1}$) were added to provide selective pressure for plasmid maintenance. Additional supplemental compounds, such as neutralized propionate or glycolate, were added to cultures where indicated in the text from 2.0 M stock solutions. Cultures were inoculated to an initial optical density at 600 nm ($OD_{600}$) of 0.05. Once the cells reached mid-exponential phase ($OD_{600}$~0.5), 50 µL of 1.0 M IPTG and 1 mL of 2.0 M neutralized propionate or glycolate was added to the cultures for induction of gene expression and to provide the substrates needed for the 3-hydroxyalkanoic acid pathway. 1 mL of culture was withdrawn daily for HPLC analysis.

Methyl Esterification of 3HV 50 mL of 3HV-containing LB microbial culture was centrifuged at 6000×g for 10 min and the supernatant was transferred to an evaporation dish for evaporating overnight in a 50° C. oven, resulting in a brown residue. To this residue, 2 mL of acidic methanol (4:1 methanol:concentrated HCl) was added and the dish was shaken for two minutes to remove 3HV from the residue. The methanol solution was transferred into a test tube, sealed, and heated at 100° C. for 3 hours. After heating, the solution was allowed to cool to room temperature. After cooling, 200 µL of the methanol solution was mixed with 1 mL of pure isopropanol in a 1.7 mL tube, vortexed, and allowed to stand for 5 minutes. Precipitate in this sample was removed by centrifugation at 13,200×g for 10 minutes. The supernatant was taken for chiral HPLC analysis.

HPLC Analyses

Achiral HPLC analysis was performed on an Agilent 1100 Series instrument equipped with an Aminex HPX-87H column (0.7 cm×30 cm) purchased from Bio-Rad Laboratories (Hercules, Calif.). For all achiral analyses, the mobile phase was 5 mM sulfuric acid, 5 µL of culture supernatant was injected for the analyses, and products were quantified using a refractive index detector. For the achiral analysis of 3HV, the column was operated at a temperature of 35.0° C. The flowrate started at 0.55 mL min$^{-1}$ and was linearly ramped up to 0.8 mL min$^{-1}$ for the first 12 minutes and maintained at 0.8 mL min$^{-1}$ for an additional 8 minutes. 3HV purchased from Epsilon Chimie (Brest, France) was used as a standard and had a retention time of approximately 14.5 min. For the analysis of DHBA and 3-HBL, the column was operated at a temperature of 40.0° C. and a constant flowrate of 0.75 mL min$^{-1}$. 3-HBL purchased from Sigma-Aldrich (St. Louis, Mo.) was used as a standard, and DHBA was prepared from 3-HBL by saponification with 10N sodium hydroxide and used as a standard. The retention times for DHBA and 3-HBL were approximately 8.9 min and 13.7 min respectively.

Chiral HPLC analysis was performed on an Agilent 1100 Series instrument equipped with a Chiralcel OD-H column (0.46 cm φ×25 cm) purchased from Daicel Chemical Industries (West Chester, Pa.). The column temperature was maintained at 40° C. Methyl-3HV was detected on a diode array detector at 210 nm. The mobile phase was 9:1 n-hexane:isopropanol and the flow rate through the column was 0.7 mL min$^{-1}$. Racemic 3HV purchased from Epsilon Chimie (Brest, France) was boiled in acidic methanol as described above to form racemic methyl-3HV, which was used as a standard. The retention times for the two enantiomers were 6.86 and 9.24 min. Prior chiral HPLC analysis with 3HB suggests that the earlier retention time is (R)-3HV, while the latter is (S)-3HV.

Mass spectrometry (MS) analysis was performed using an Agilent 6120 Quadrupole LC/MS unit operated in positive ion electrospray mode. The LC mobile phase was 25 mM ammonium formate, pH 2, and the flowrate was 0.6 mL min$^{-1}$. The unit was operated downstream of the liquid chromatography column described above under the same chromatography conditions. Samples were vaporized at 150° C. and nitrogen at 300° C., 60 psig, and 5.0 L min$^{-1}$ was used as the carrier gas for MS analysis. The ion detector was calibrated to scan for cations at an m/z of 138, representing the ammonium adduct of DHBA and 120 for the ammonium adduct of 3-HBL.

```
Sequence of M. elsdenii pct gene (SEQ ID NO: 9):
atgagaaaagtagaaatcattacagctgaacaagcagctcagctcgta aaagacaacgacacgattacgtctatcggctttgtcagcagcgcccat ccggaagcactgaccaaagctttggaaaaacggttcctggacacgaac accccgcagaacttgacctacatctatgcaggctctcagggcaaacgc gatggccgtgccgctgaacatctggcacacacaggccttttgaaacgc gccatcatcggtcactggcagactgtaccggctatcggtaaactggct gtcgaaaacaagattgaagcttacaacttctcgcagggcacgttggtc cactggttccgcgccttggcaggtcataagctcggcgtcttcaccgac atcggtctggaaactttcctcgatccccgtcagctcggcggcaagctc aatgacgtaaccaaagaagacctcgtcaaactgatcgaagtcgatggt catgaacagcttttctacccgaccttcccggtcaacgtagctttcctc cgcggtacgtatgctgatgaatccggcaatatcaccatggacgaagaa atcgggcctttcgaaagcacttccgtagcccaggccgttcacaactgt ggcggtaaagtcgtcgtccaggtcaaagacgtcgtcgctcacggcagc ctcgacccgcgcatggtcaagatccctggcatctatgtcgactacgtc gtcgtagcagctccggaagaccatcagcagacgtatgactgcgaatac gatccgtccctcagcggtgaacatcgtgctcctgaaggcgctaccgat gcagctctccccatgagcgctaagaaaatcatcggccgccgcggcgct ttggaattgactgaaaacgctgtcgtcaacctcggcgtcggtgctccg gaatacgttgcttctgttgccggtgaagaaggtatcgccgataccatt accctgaccgtcgaaggtggcgccatcggtggcgtaccgcagggcggt gcccgcttcggttcgtcccgcaatgccgatgccatcatcgaccacacc tatcagttcgacttctacgatggcggcggtctggacatcgcttacctc ggcctggcccagtgcgatggctcgggcaacatcaacgtcagcaagttc ggtactaacgttgccggctgcggcggtttccccaacatttcccagcag acaccgaatgtttacttctgcggcaccttcacggctggcggcttgaaa atcgctgtcgaagacggcaaagtcaagatcctccaggaaggcaaagcc aagaagttcatcaaagctgtcgaccagatcactttcaacggttcctat gcagcccgcaacggcaaacacgttctctacatcacagaacgctgcgta tttgaactgaccaaagaaggcttgaaactcatcgaagtcgcaccgggc atcgatattgaaaaagatatcctcgctcacatggacttcaagccgatc attgataatccgaaactcatggatgcccgcctcttccaggacggtccc atgggactgaaaaaat
```

References

Boynton, Z. L., Bennett, G. N., and Rudolph, F. B. (1996). Cloning, sequencing, and expression of genes encoding phosphotransacetylase and acetate kinase from *Clostridium acetobutylicum* ATCC 824. Appl. Environ. Microbiol., 62:2758-2766.

Carey, F. A. (2000). Organic Chemistry. $4^{rd}$ ed., McGraw Hill, New York, N.Y.

Chen, G. Q. and Wu, Q. (2005). Microbial production and applications of chiral hydroxyalkanoates. Appl. Microbiol. Biotechnol., 67:592-599.

Chiba, T. and Nakai, T. A. (1985). Synthetic approach to (1)-thienamycin from methyl (R)-(2)-3-hydroxybutanoate. A new entry to (3R,4R)-3-[(R)-1-hydroxyethyl-4-acetoxy-2-azetidinone. Chem. Lett., 5:651-654.

Datsenko, K. A. and Wanner, B. L. (2000). One-step inactivation of chromosomal genes in *Escherichia coli* K-12 using PCR products. Proc. Natl. Acad. Sci. USA, 97:6640-6645.

Gao, H. J., Wu, Q. and Chen, G. Q. (2002). Enhanced production of D-(−)-3-hydroxybutyric acid by recombinant *Escherichia coli*. FEMS Microbiol. Lett., 2002, 213:59-65.

Huisman, G. W., Wonink, E., Meima, R., Kazemier, B., Terpstra, P., and Witholt, B. (1991). Metabolism of Poly(3-hydroxyalkanoates) (PHAs) by *Psuedomonas oleovorans*. J. Biol. Chem. 266:2191-2198.

Kim, E. E., Baker, C. T., Dwyer, M. D., Murcko, M. A., Rao, B. G., Tung, R. D., and Navia, M. A. (1995). Crystal structure of HIV-1 protease in complex with VX-478, a potent and orally bioavailable inhibitor of the enzyme. J. Am. Chem. Soc., 117:1181-1182.

Lee, S. H. and Park, O.-J. (2009). Uses and production of chiral 3-hydroxy-γ-butyrolactones and structurally related chemicals. Appl. Microbiol. Biotechnol., 84:817-828.

Lee, S. H., Park, O.-J., and Uh, H.-S. (2008). A chemoenzymatic approach to the synthesis of enantiomerically pure (S)-3-hydroxy-γ-butyrolactone. Appl. Microbiol. Biotechnol., 79:355-362.

Lee, S. Y., Park, J. H., Jang, S. H., Nielsen, L. K., Kim, J., and Jung, K. S. (2008). Fermentive Butanol Production by Clostridia. Biotechnol. Bioeng., 101:209-228.

Lee, S. Y., Park, S. H., Lee, Y., and Lee, S. H. (2002). Production of chiral and other valuable compounds from microbial polyesters. In: Dio, Y., Steinbüchel, A. (eds.) Biopolymers, polyesters III. Wiley-VCH, Weinheim, pp. 375-387.

Liu, Q., Ouyang, S. P., Chung, A., Wu, Q. and Chen, G. Q. (2007). Microbial production of R-3-hydroxybutyric acid by recombinant *E. coli* harboring genes of phbA, phbB, and tesB. Appl. Microbiol. Biotechnol. 76:811-818.

Liu, S. J. and Steinbüchel, A. (2000a). A novel genetically engineered pathway for synthesis of poly(hydroxyalkanoic acids) in *Escherichia coli*. Appl. Environ. Microbiol. 66:739-743.

Liu, S. J. and Steinbüchel, A. (2000b). Exploitation of butyrate kinase and phosphotransbutyrylase from Clostridium acetobutylicum for the in vitro biosynthesis of poly(hydroxyalkanoic acid). Appl. Microbiol. Biotechnol. 53:545-552.

Naggert, J., Narasimhan, M. L., DeVeaux, L., Cho, H., Randhawa, Z. I., Cronan, J. E., Green, B. N. and Smith, S. (1991). Cloning, sequencing, and characterization of *Escherichia coli* thioesterase II. J. Biol. Chem. 266:11044-11050.

Nunez, M. F., Pellicer, M. T., Badia, J., Aguilar, J., and Baldoma, L. (2001). Biochemical characterization of the 2-ketoacid reductases encoded by ycdW and yiaE genes in *Escherichia coli*. Biochem. J., 354:707-715.

Park, S. H., Lee, S. H., and Lee, S. Y. (2001). Preparation of optically active β-aminoacids from microbial polyester polyhydroxyalkanoates. J. Chem. Res. Synop., 11:498-499.

Peoples, O. P. and Sinskey, A. J. (1989). Poly-β-hydroxybutyrate biosynthesis in *Alcaligenes eutrophus* H16: characterization of the genes encoding β-ketothiolase and acetoacetyl-CoA reductase. J. Biol. Chem., 264, 15293-15297.

Sambrook, J. and Russell, D. W. (2001). Molecular Cloning: a Laboratory Manual. $3^{rd}$ Ed., Cold Spring Harbor Laboratory, Cold Spring Harbor, N.Y.

Schubert, P., Steinbüchel, A., and Schlegel, H. G. (1988). Cloning of the *Alcaligenes eutrophus* genes for synthesis of poly-beta-hydroxybutyric acid (PHB) and synthesis of PHB in *Escherichia coli*. J. Bacteriol., 170:5837-5847.

Schweiger, G. and Buckel, W. (1984). On the dehydration of (R)-lactate in the fermentation of alanine to propionate by *Clostridium propionicum*. FEBS Lett., 171:79-84.

Seebach, D., Albert, M., Arvidsson, P. I., Rueping, M., and Schreiber, J. V. (2001). From the biopolymer PHB to biological investigations of unnatural β- and γ-peptides. Chimia, 55:345-353.

Slater, S., Houmiel, K. L., Tran, M., Mitsky, T. A., Taylor, N. B., Padgette, S. R., and Gruys, K. J. (1998). Multiple β-ketothiolases mediate poly(β-hydroxyalkanoate) copolymer synthesis in *Ralstonia eutropha*. J. Bacteriol., 180:1979-1987.

Stim-Herndon, K. P., Petersen, D. J., and Bennett, G. N. (1995). Molecular characterization of the acetyl coenzyme A acetyltransferase (thiolase) from *Clostridium acetyobutylicium* ATCC 824. Gene, 154:81-85.

Taguchi, S., Yamada, M., Matsumoto, K. Tajima, K., Satoh, Y., Masanobu, M., Ohno, K. Kohda, K., Shimamura, T., Kambe, H., and Shusei, O. (2008). A microbial factory for lactate-based polyesters using a lactate-polymerizing enzyme. Proc. Natl. Acad. Sci., 105:17323-17327.

Tseng, H.-C., Martin, C., Nielsen, D., and Prather, K. L. J. (2009). Metabolic Engineering of *Escherichia coli* for Enhanced Production of (R)- and (S)-3-Hydroxybutyrate. Appl. Environ. Microbiol., 75:3137-3145.

Wang, G. and Hollingsworth, R. I. (1999a). Direct conversion of (S)-3-hydroxy-γ-butyrolactone to chiral three carbon building blocks. J. Org. Chem., 64:1036-1038.

Wang, G. and Hollingsworth, R. I. (1999b). Synthetic routes to L-carnitine and L-gamma-amino-beta hydroxybutyric acid from (S)-3-hydroxy-γ-butyrolactone by functional group priority switching. Tetrahedron Asymmetry, 10:1895-1901.

Werpy, T. and Petersen, G.: Top value added chemicals from biomass, Vol 1: results of screening for potential candidates from sugars and synthesis gas. Oak Ridge, Tenn.: U.S. Department of Energy, August 2004.

Yasohara Y, Kizaki N, Hasegawa J, Wada M, Kataoka M, Shimizu S. Molecular cloning and overexpression of the gene encoding an NADPH-dependent carbonyl reductase from *Candida magnoliae*, involved in stereoselective reduction of ethyl 4-chloro-3-oxobutanoate. Biosci Biotechnol Biochem. 2000 July; 64(7):1430-6.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

Equivalents

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety, particularly for the disclosure referenced herein.

What is claimed is:

1. An isolated cell that recombinantly expresses (1) a pct gene, encoding a propionyl-CoA transferase enzyme (2) at least one of a phaA, thil, atoB or bktB gene, encoding a thiolase enzyme (3) at least one of a phaB or hbd gene, encoding a reductase enzyme, and (4) a tesB gene, encoding a thioesterase B enzyme, wherein the isolated recombinant cell can produce a cell culture that contains at least 200 mg $L^{-1}$ 3,4-dihydroxybutyrate (DHBA) or at least 10 mg $L^{-1}$ 3-hydroxybutyrolactone (3-HBL).

2. The isolated cell of claim 1 wherein the cell further recombinantly expresses a gene encoding for glycolate reductase.

3. The isolated cell of claim 1 wherein the cell is a bacterial cell, a fungal cell, a plant cell, an insect cell or an animal cell.

4. A method for producing DHBA or 3-HBL, the method comprising culturing the isolated cell of claim 1 to produce DHBA or 3-HBL.

5. The method of claim 4, further comprising recovering the DHBA or 3-HBL from the cell culture.

6. The method of claim 4 wherein the cell is cultured in the presence of glycolate.

7. A cell culture produced by culturing the isolated cell of claim 1.

8. The cell culture of claim 7, wherein the cell culture contains at least 200 mg $L^{-1}$ DHBA.

9. The cell culture of claim 7, wherein the cell culture contains at least 10 mg $L^{-1}$ 3-HBL.

10. A supernatant of a cell culture produced by culturing the isolated cell of claim 1.

11. The supernatant of claim 10, wherein the supernatant contains at least 200 mg $L^{-1}$ DHBA.

12. The supernatant of claim 10, wherein the supernatant contains at least 10 mg $L^{-1}$ 3-HBL.

13. The supernatant of claim 10 wherein the supernatant is subjected to lactonization.

14. The supernatant of claim 13 wherein lactonization is achieved through acidification to reduce the pH of the supernatant.

15. The supernatant of claim 13 wherein lactonization is achieved through auto-lactonization of DHBA-CoA.

16. A method for producing an isolated cell that has increased 3,4-dihydroxybutyrate (DHBA) or 3-hydroxybutyrolactone (3-HBL) production comprising recombinantly expressing (1) a pct gene, encoding a propionyl-CoA transferase enzyme (2) at least one of a phaA, thil, atoB or bktB gene, encoding a thiolase enzyme (3) at least one of a phaB or hbd gene, encoding a reductase enzyme, and (4) a tesB gene, encoding a thioesterase B enzyme in the cell.

17. The method of claim 16 wherein the isolated cell further recombinantly expresses a gene encoding for glycolate reductase.

18. The method of claim 16 wherein the isolated cell is a bacterial cell, a fungal cell, a plant cell, an insect cell or an animal cell.

19. The isolated cell of claim 3, wherein the fungal cell is a yeast cell.

20. The method of claim 18, wherein the fungal cell is a yeast cell.

* * * * *